US009232905B2

United States Patent
Adachi et al.

(10) Patent No.: US 9,232,905 B2
(45) Date of Patent: Jan. 12, 2016

(54) UNCOMFORTABLE LOUDNESS LEVEL ESTIMATING SYSTEM, UNCOMFORTABLE LOUDNESS LEVEL ESTIMATING DEVICE, UNCOMFORTABLE LOUDNESS LEVEL ESTIMATING METHOD, AND COMPUTER PROGRAM FOR SAME

(71) Applicant: Panasonic Corporation, Osaka (JP)

(72) Inventors: Shinobu Adachi, Nara (JP); Koji Morikawa, Kyoto (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 323 days.

(21) Appl. No.: 14/027,905

(22) Filed: Sep. 16, 2013

(65) Prior Publication Data

US 2014/0072127 A1  Mar. 13, 2014

Related U.S. Application Data

(63) Continuation of application No. PCT/JP2012/006612, filed on Oct. 16, 2012.

(30) Foreign Application Priority Data

Oct. 18, 2011  (JP) ................................. 2011-228574

(51) Int. Cl.
*A61B 5/0484* (2006.01)
*A61B 5/00* (2006.01)
(Continued)

(52) U.S. Cl.
CPC ............. *A61B 5/04845* (2013.01); *A61B 5/125* (2013.01); *A61B 5/726* (2013.01); *A61B 5/7267* (2013.01); *H04R 25/70* (2013.01); *H04R 29/00* (2013.01)

(58) Field of Classification Search
None
See application file for complete search history.

(56) References Cited

U.S. PATENT DOCUMENTS

2001/0049480 A1  12/2001  John et al.
2009/0163828 A1   6/2009  Turner et al.
(Continued)

FOREIGN PATENT DOCUMENTS

JP      2010-504139 T      2/2010
WO   WO 2008/038650 A1   4/2008
(Continued)

OTHER PUBLICATIONS

Lightfoot et al "Cortical Electric Response Audiometry Hearing Threshold Estimation: Accuracy, Speed, and the Effects of Stimulus Presentation Features." Ear&Hearing vol. 27 Issue 5. Oct. 2006. pp. 443-456.*

(Continued)

*Primary Examiner* — Curtis Kuntz
*Assistant Examiner* — Qin Zhu
(74) *Attorney, Agent, or Firm* — Renner, Otto, Boisselle & Sklar, LLP

(57) ABSTRACT

An uncomfortable sound pressure estimation system includes: a biological signal measurement section for measuring an electroencephalogram signal of a user; a sound stimulation output section for presenting a sound stimulation group to the user, the sound stimulation group including a first sound, a second sound, and a third sound which are pure tones of the same frequency and which consecutively decrease in sound pressure within a predetermined range; an extraction section for, from the electroencephalogram signal in a predetermined zone defined based on a point of presenting at least one of the second sound and the third sound as a starting point, extracting an N1-P2-amplitude related or wavelet-coefficient related characteristic amount of event-related potential of the electroencephalogram signal; and a determination section for determining an uncomfortable sound pressure at the frequency of the sound stimulation group based on the characteristic amount extracted by the extraction section.

17 Claims, 16 Drawing Sheets

(51) Int. Cl.
*A61B 5/12* (2006.01)
*H04R 29/00* (2006.01)
*H04R 25/00* (2006.01)

(56) References Cited

U.S. PATENT DOCUMENTS

2010/0076338 A1 3/2010 Kwak
2010/0202642 A1 8/2010 LoPresti et al.
2012/0072213 A1 3/2012 Adachi et al.

FOREIGN PATENT DOCUMENTS

WO WO 2009/149378 A1 12/2009
WO WO 2011/093005 A1 8/2011

OTHER PUBLICATIONS

Haab, L.; Wallhausser-Franke, E.; Trenado, C.; Strauss, D.J., "Modeling limbic influences on habituation deficits in chronic tinnitus aurium," Engineering in Medicine and Biology Society, 2009. EMBC 2009. Annual International Conference of the IEEE , vol., No., pp. 4234,4237, Sep. 3-6, 2009 doi: 10.1109/IEMBS.2009. 5332696.*
International Search Report for corresponding International Application No. PCT/JP2012/006612 mailed Jan. 8, 2013.
Takashi Kimitsuki et al., "Inner ear auditory testing in patients with normal hearing showing hyperacusis", Audiology Japan 52, pp. 152-156, 2009 and concise explanation.
Thornton, A.R. et al., "The objective estimation of loudness discomfort level using auditory brainstem evoked responses", Scan. Audiol. 1987; 16(4):219-25 (Abstract).
Jishoukanrendeni (ERP) Manyuaru—P300 WO Chushinni—(or "Event-Related Potential (ERP) Manual—mainly concerning P300—"), edited by Kimitaka Kaga et al., Shinohara Shuppan Shinsha, 1995, p. 30 and concise explanation.
D.P. Pascoe, "Clinical measurements of the auditory dynamic range and their relation to formulas for hearing aid gain. In lensen". H. I. (Ed.) Hearing Aid Fitting: Theoretical and Practical Views 13th Danavox Symposium. Copenhagen: Stougaard. (1988).
Chinese Search Report dated May 6, 2015 and English translation thereof for corresponding Chinese Application No. 201280004721.9.
Mai Mariam et al., "Detection of the uncomfortable loudness level by electroencephalographic data: A novelty detection approach using habituation correlates", Engineering in Medicine and Biology Society, 2008, 30th Annual International Conference of the IEEE, Piscataway, NJ USA, Aug. 20, 2008, pp. 4976-4979, XP031509131.
Mariam M. et al., "Differentiation of perceived sound levels by electroencephalographic data: A novelty detection approach using habituation correlates", Neural Engineering, 2009, 4th International IEEE/EMBS Conference on IEEE, Piscataway, NJ USA, Apr. 29, 2009, pp. 570-573, XP031478400.
Schafer et al., "Cortical augmenting in alexithymic subjects after unpleasant acoustic stimulation", Journal of Psychosomatic Research, Pergamon Press, London, US, vol. 63, No. 4, Oct. 1, 2007, pp. 357-364, XP022296770.
Shinobu Adachi et al., "Estimating uncomfortable loudness levels using evoked potentials to auditory stimuli for hearing and fitting", The Effect of Applied Compressive Loading on Tissue-Engineered Cartilage Constructs Cultured with TGF-BETA3, IEEE, Aug. 28, 2012, pp. 2108-2111, XP032463355.
Mai Mariam et al., "Feasibility of N1-P2 habituation to differentiate loudness levels", Biomedical Engineering (ICOBE), 2012 International Conference on, IEEE, Feb. 27, 2012, pp. 94-98, XP032157355.
Nobuo Adachi et al., "Jun'on Pair Shigeki ni Taisuru Yuhatsu Den'i ni Modozuku Fukai on'atsu Level Suitei", Japanese Journal of Clinical Neurophysiology, Oct. 1, 2011, vol. 39, No. 5, p. 447.
Extended European Search Report for corresponding European Application No. 12841646.8 dated Feb. 25, 2015.

* cited by examiner

FIG.1

|   | RIGHT | | | LEFT | | |
|---|---|---|---|---|---|---|
|   | 1000 | 2000 | 4000 | 1000 | 2000 | 4000 |
| 1 | 92.5 | 87.5 | 90 | 92.5 | 87.5 | 90 |
| 2 | 107.5 | 105 | 105 | 110 | 110 | 110 |
| 3 | 110 | 110 | 110 | 110 | 110 | 110 |
| 4 | 92.5 | 95 | 95 | 85 | 80 | 82.5 |
| 5 | 107.5 | 107.5 | 102.5 | 105 | 102.5 | 102.5 |
| 6 | 107.5 | 110 | 100 | 97.5 | 102.5 | 110 |
| 7 | 100 | 100 | 95 | 95 | 92.5 | 90 |
| 8 | 107.5 | 110 | 110 | 105 | 105 | 105 |
| 9 | 95 | 95 | 90 | 102.5 | 97.5 | 95 |
| 10 | 97.5 | 95 | 90 | 90 | 90 | 85 |
| 11 | 110 | 107.5 | 110 | 105 | 97.5 | 107.5 |
| 12 | 97.5 | 97.5 | 95 | 92.5 | 87.5 | 85 |
| 13 | 90 | 87.5 | 87.5 | 85 | 82.5 | 82.5 |
| 14 | 92.5 | 92.5 | 92.5 | 90 | 90 | 90 |
| 15 | 92.5 | 92.5 | 82.5 | 92.5 | 90 | 87.5 |
| AVERAGE | 100.0 | 99.5 | 97.0 | 97.2 | 95.0 | 95.5 |
| STANDARD DEVIATION | 7.2 | 7.9 | 8.5 | 8.2 | 9.1 | 10.4 |

UPPER VIEW    FRONTAL VIEW

FIG.6

| PARTICIPANT | SOUND STIMULATION GROUP | | SUBJECTIVE UCL VALUE | FIRST SOUND | SECOND SOUND | THIRD SOUND |
|---|---|---|---|---|---|---|
| | RIGHT/LEFT | FREQUENCY | | | | |
| 01 | RIGHT | 1000Hz | 92.5 | 1.84 | 0.24 | -0.73 |
| | | 2000Hz | 87.5 | 1.26 | -0.42 | 1.56 |
| | | 4000Hz | 90 | 0.84 | 0.68 | -1.71 |
| | LEFT | 1000Hz | 92.5 | -0.79 | 0.89 | 1.50 |
| | | 2000Hz | 87.5 | 0.73 | -0.94 | -1.45 |
| | | 4000Hz | 90 | -0.60 | 0.06 | 0.09 |
| 02 | RIGHT | 1000Hz | 107.5 | -0.95 | 1.04 | 0.54 |
| | | 2000Hz | 105 | 1.22 | -0.06 | 0.18 |
| | | 4000Hz | 105 | 0.91 | 0.52 | -0.18 |
| | LEFT | 1000Hz | 110 | -1.14 | 0.63 | -0.11 |
| | | 2000Hz | 110 | -1.45 | -0.51 | -1.05 |
| | | 4000Hz | 110 | -0.54 | 0.55 | -0.54 |
| 03 | RIGHT | 1000Hz | 110 | 1.54 | -0.06 | 0.49 |
| | | 2000Hz | 110 | 0.47 | 0.93 | 1.47 |
| | | 4000Hz | 110 | -1.04 | 0.93 | 0.66 |
| | LEFT | 1000Hz | 110 | 1.42 | 0.24 | -0.07 |
| | | 2000Hz | 110 | 1.19 | -1.45 | 0.71 |
| | | 4000Hz | 110 | -0.21 | 0.64 | -0.66 |
| 04 | RIGHT | 1000Hz | 92.5 | -0.16 | -1.57 | -0.87 |
| | | 2000Hz | 95 | 0.50 | 1.26 | -2.47 |
| | | 4000Hz | 95 | -0.44 | -0.91 | 0.99 |
| | LEFT | 1000Hz | 85 | -0.54 | -0.18 | -1.80 |
| | | 2000Hz | 80 | 0.66 | -2.18 | -0.49 |
| | | 4000Hz | 82.5 | -0.10 | -1.56 | -1.33 |
| ... | ... | ... | | | | |

FIG.11

|  | 250Hz | 500Hz | 1000Hz | 2000Hz | 4000Hz |
|---|---|---|---|---|---|
| RIGHT | 30 | 35 | 40 | 50 | 55 |
| LEFT | 25 | 30 | 40 | 45 | 50 |

FIG.12

UNCOMFORTABLE SOUND PRESSURE (dBHL)

|  | 1000 Hz | 2000 Hz | 4000 Hz |
|---|---|---|---|
| RIGHT | 105 | 100 | 100 |
| LEFT | 100 | 95 | 100 |

FIG.15

| HTL VALUE dBHL | ESTIMATED UCL VALUE dBHL |
|---|---|
| 0 | 97 |
| 5 | 99 |
| 10 | 99 |
| 15 | 98 |
| 20 | 97 |
| 25 | 101 |
| 30 | 102 |
| 35 | 101 |
| 40 | 103 |
| 45 | 105 |
| 50 | 107 |
| 55 | 108 |
| 60 | 110 |
| 65 | 114 |
| 70 | 115 |
| 75 | 117 |
| 80 | 120 |
| 85 | 120 |
| 90 | 124 |
| 95 | 130 |
| 100 | 127 |

*FIG.18*

|  | SECOND SOUND | THIRD SOUND |
|---|---|---|
| 1000Hz | 2.23 | 1.22 |
| 2000Hz | 1.28 | 0.94 |
| 4000Hz | 1.37 | 0.70 |

UNCOMFORTABLE LOUDNESS LEVEL ESTIMATING SYSTEM, UNCOMFORTABLE LOUDNESS LEVEL ESTIMATING DEVICE, UNCOMFORTABLE LOUDNESS LEVEL ESTIMATING METHOD, AND COMPUTER PROGRAM FOR SAME

This is a continuation of International Application No. PCT/JP2012/006612, with an international filing date of Oct. 16, 2012, which claims priority of Japanese Patent Application No. 2011-228574, filed on Oct. 18, 2011, the contents of which are hereby incorporated by reference.

TECHNICAL FIELD

The present disclosure relates to a technique of evaluating whether a speech sound has been heard in comfort. More specifically, the present disclosure relates to a technique of estimating an uncomfortable sound pressure with respect to a pure tone, in the context of "fitting" of a hearing aid or the like, i.e., adjusting an amount of amplification for each frequency of an external sound to arrive at a sound of a loudness which is appropriate to each individual user.

DESCRIPTION OF THE RELATED ART

In recent years, people suffering from presbycusis are increasing in number due to the aging society. Due to the increased opportunities for listening to loud music for long hours as well as other influences, there is an increasing number of young people suffering from hypacusia associated with acoustic traumas. Moreover, due to the downsizing and improved performance of hearing aids, users have come to wear hearing aids with less of a psychological barrier. This has led to an increasing number of users wearing hearing aids.

A user suffering from hypacusia has difficulty in hearing sounds of a specific frequency(s). This specific frequency varies from user to user. A hearing aid amplifies the amplitude of a sound signal at this specific frequency, thus making it easier for the user to hear sounds.

A hearing aid is required to change the amount by which it amplifies sounds, in accordance with the level of deterioration in the hearing of the user. Therefore, before beginning use of a hearing aid, "fitting" is required for adjusting the amount of sound amplification in accordance with the hearing of each user.

The purpose of fitting is to keep the output sound pressure of a hearing aid at an MCL (most comfortable level). As used herein, the "output sound pressure" of a hearing aid refers to the fluctuations in air pressure that are perceivable to humans as a sound. The MCL defines a sound pressure which guarantees comfortable hearing by the user. The hearing aid needs to ensure that the output sound pressure satisfies MCL for each sound frequency.

Examples of inappropriate fitting may be: (1) an insufficient amount of amplification for sound pressure; or (2) an excessive amount of amplification for sound pressure. For example, if the amount of amplification for sound pressure is insufficient, the user cannot aurally distinguish audios. In this case, the aforementioned purpose of using a hearing aid is not met. If the amount of amplification for sound pressure is excessive, the user is capable of aural distinction of audios, but may find the audio to be loud, which prevents the user from using the hearing aid over a long time. Therefore, a fitting of a hearing aid needs to be done in such a manner that neither (1) nor (2) occurs. Especially (2) possesses a possibility that the hearing aid may present an audio with an unduly high sound pressure to the user. This has created danger of hurting the user's ear with audios having high sound pressure.

Fitting generally comes into two steps. A first step of fitting is measuring an audiogram. An "audiogram" refers to a measurement of a threshold value (hearing threshold level: HTL) defining the smallest sound pressure of a pure tone that allows it to be heard by a user. An audiogram may be, for example, a diagram in which such a threshold value (decibel value) is plotted for different frequencies (e.g., 250 Hz, 500 Hz, 1000 Hz, 2000 Hz, 4000 Hz).

A second step of fitting is determining an amount of amplification for sound pressure. For example, by using a mathematical function (called a fitting theory) for estimating an amount of sound amplification, an amount of amplification is determined for each frequency and for each sound pressure of an input sound. There are a number of types of fitting theories, for example: the half-gain method, in which an insertion gain of each frequency is made half of the threshold value of that frequency; Berger's method, which slightly augments the amplify from 1000 Hz to 4000 Hz by taking into consideration the frequency band and level of conversational voices; the POGO method which, based on the half-gain method, reduces the gains at 250 Hz and 500 Hz (where there is not so much speech sound information but a lot of noise component is included) by 10 dB and 5 dB, respectively; and the NAL-R method, which performs amplification so that a frequency of long-term sound analysis of words will fall around a comfortable level.

Moreover, the "fitting theory" is also inclusive of a method of determining an amount of amplification for sound pressure by utilizing the information of a threshold value, a UCL (uncomfortable level; which may also be referred to as "uncomfortable sound pressure" hereinafter) which is a high sound pressure level that is felt uncomfortable to the user, and the MCL. In that case, before determining an amount of amplification for sound pressure, the UCL and MCL are either measured or estimated. In order to avoid problem (2) above, it is necessary to measure the UCL, and set an amount of amplification in a range such that the UCL is not exceeded.

Similarly to audiogram measurement, a UCL is to be measured for each frequency. Conventionally, the UCL is measured based on subjective reporting. "Subjective reporting" involves, after a user hears a sound, the user making a subjective account as to how the sound was felt to him or her. For example, while using an audiometer, continuous sounds or discontinuous sounds are presented to the user by using an ascending method (i.e., the sound pressure level is gradually increased), and the user is asked to report whether the sound pressure is so loud that he or she cannot tolerate hearing it for a long time. Then, a sound pressure beyond which the user cannot retain tolerance over a long time, according to their own reporting, is defined as a UCL (Takashi KIMITSUKI et al., "Inner ear auditory testing in patients with normal hearing showing hyperacusis", Audiology Japan, Vol. 52, No. 3, P. 152-156, 2009 (hereinafter referred to as "Non-Patent Document 1").

An UCL measurement through subjective reporting is difficult because the UCL criterion will fluctuate under individual influences or the influences of linguistic expressions, and thus there is no established technique. Therefore, methods of taking an objectively measurement of UCL by using electroencephalogram are under development. For example, in a technique disclosed in Thornton, A. R., et al., "The objective estimation of loudness discomfort level using auditory brainstem evoked responses", Scandinavian Audiology, Vol. 16, No. 4, P. 219-225, 1987 (hereinafter referred to as "Non-Patent Document 2"), a UCL is estimated based on a relationship between the stimulation intensity and the latency of a V wave that is contained in a brainstem response called ABR (auditory brainstem response). As the sound pressure increases, the V wave latency decreases. The sound pressure of the sound which the user was hearing when the decrease in V wave latency became saturated is identified. A sound pressure which is obtained by adding a constant (e.g., 15 or 10) to this identified sound pressure is defined as the UCL.

On the other hand, the MCL (most comfortable level) is generally difficult to measure through subjective reporting, and therefore is often approximated as a gradient corresponding to a half of the hearing threshold value (half gain) or as a median between the UCL and the hearing threshold value.

SUMMARY

In the aforementioned conventional techniques, it has been necessary to determine the UCL of a user while keeping the user out of an uncomfortable state as much as possible.

A non-limiting and illustrative embodiment of the present disclosure provides a technique which enables estimation of an uncomfortable sound pressure of a user without presenting an overbearing sound to the user.

In one general aspect, an uncomfortable sound pressure estimation system disclosed herein comprises: a biological signal measurement section configured to measure an electroencephalogram signal of a user; a sound stimulation output section configured to present a sound stimulation group to the user, the sound stimulation group including a first sound, a second sound, and a third sound which are pure tones of a same frequency and which consecutively decrease in sound pressure within a predetermined range; an extraction section configured to extract, from the electroencephalogram signal in a predetermined zone defined based on a point of presenting at least one of the second sound and the third sound as a starting point, an N1-P2-amplitude related or wavelet-coefficient related characteristic amount of event-related potential of the electroencephalogram signal; and a determination section configured to determine an uncomfortable sound pressure at the frequency of the sound stimulation group based on the characteristic amount extracted by the extraction section.

According to the above aspect, without allowing a user to hear any sound that is so overbearing that it is felt uncomfortable, a UCL can be estimated which is necessary for hearing aid adjustment. Thus, the user's burden in hearing aid adjustment can be reduced.

The general and specific embodiment above can be implemented as a system, a method, or a computer program, or implemented by using a combination of a system, a method, and/or a computer program.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF DRAWINGS

FIG. 1 shows subjectively-reported values of uncomfortable sound pressure obtained in a subjective report experiment conducted by the inventors.

FIG. 6 shows an example of training data used in an uncomfortable sound pressure estimation conducted by the inventors.

FIG. 11 shows exemplary data which is input to an HTL input section.

FIG. 12 shows an example of result accumulation in a result accumulating database (DB).

FIG. 15 shows exemplary UCL values to be estimated from HTLs.

FIG. 18 shows exemplary threshold values for N1-P2 amplitude in response to a second sound and a third sound, with respect to different frequencies.

DETAILED DESCRIPTION

Figure 2:
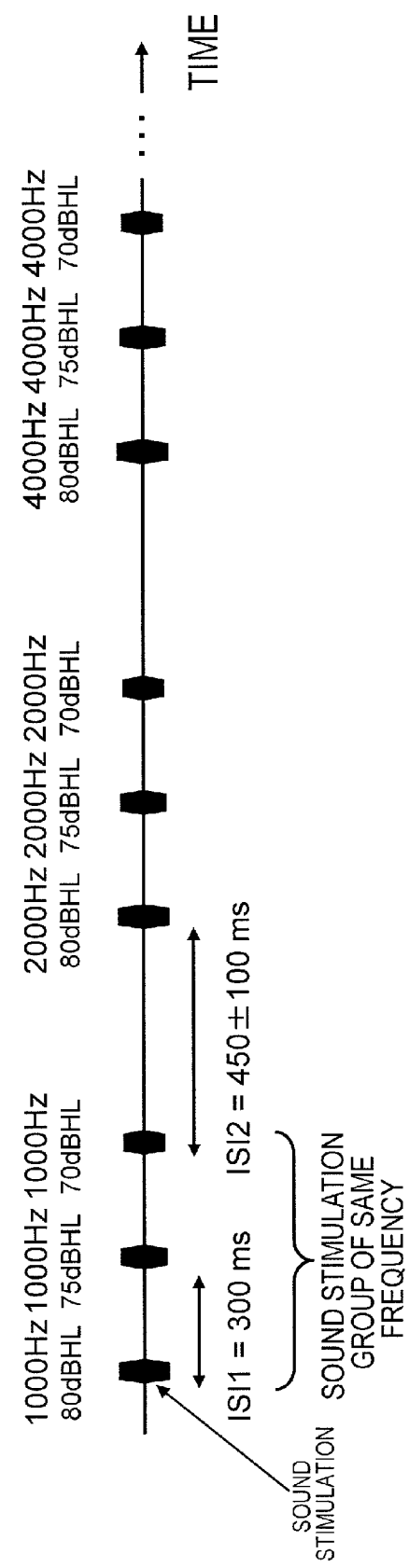
FIG. 2 shows a sound stimulation construction used in an electroencephalographic experiment conducted by the inventors.

The conventional techniques disclosed in Non-Patent Document 1 and Non-Patent Document 2 above adopt a method which, after a user is placed in an uncomfortable state by presenting a sound stimulation with sound pressure of an uncomfortable level to the user, determines whether the sound pressure of that sound stimulation is the UCL or not. In other words, an approach of examining an uncomfortable sound pressure based on whether the user is in an uncomfortable state or not is adopted. Therefore, in order to conduct a hearing evaluation, an overbearing sound must be presented to the user, and the user actually needs to be thus placed in an uncomfortable state.

Hereinafter, with reference to the attached drawings, embodiments of the uncomfortable sound pressure estimation system according to the present disclosure will be described.

First, the definitions of the terms used in the present specification will be described.

An "event-related potential (ERP)" is a fluctuation in the potential of an electroencephalogram (EEG) that occurs in response to a stimulation.

A "sound stimulation", also referred to as an auditory stimulation, is a sound which is presented to a User.

An "N1 component" is a negative potential which is induced at about 100 ms since the point of presenting a sound stimulation as a starting point.

A "P2 component" is a positive potential which is induced at about 200 ms since the point of presenting a sound stimulation as a starting point. The N1 component and the P2 component are contained in an event-related potential.

"Latency" is the time, based on the point of presenting an audio stimulation as a starting point, until a peak potential of a positive component or a negative component appears.

A "negative component" generally refers to a potential which is smaller than 0 µV.

A "positive component" generally refers to a potential which is greater than 0 µV.

An "uncomfortable sound pressure (uncomfortable loudness level: UCL)" is a sound pressure which is so loud that it is felt uncomfortable to a user.

A "hearing threshold level (HTL)" is the sound pressure of a softest sound that is audible to a user, which may simply be referred to as a threshold value.

"Presenting a sound" means outputting a pure tone.

A "pure tone" is a tone which repetitively undergoes periodic oscillation, such that it is expressed as a sine wave having only one frequency component.

In the present specification, in order to define a component of an event-related potential, a point in time after the lapse of a predetermined time since a given point is expressed by referring to a "latency of about 100 ms", for example. This means possible inclusion of a range around the specific point of 100 ms. Generally speaking, there are 30 to 50 ms of differences (shifts) in event-related potential waveform between individuals, according to table 1 on p. 30 of "JISHOUKANRENDENI (ERP) MANYUARU—P300 WO CHUSHINNI—(or "Event-Related Potential (ERP) Manual—mainly concerning P300—"), edited by Kimitaka KAGA et al., Shinohara Shuppan Shinsha, 1995)". Therefore, the terms "about X ms" and "near X ms" mean that a breadth of 30 to 50 ms may exist before or after X ms (e.g., 100 ms±30 ms, 200 ms±50 ms).

According to the present disclosure, a sound stimulation of a sound pressure that does not constitute an uncomfortable sound pressure for the user is presented; an induced electroencephalographic response to the presented sound is measured; and based on a result of analyzing the induced electroencephalographic response, a UCL of that user is estimated. As a result, without allowing the user to hear an overbearing sound that would be felt uncomfortable, the UCL of that user can be estimated.

The following is an outline of an embodiment(s) of the present invention.

An uncomfortable sound pressure estimation system according to an embodiment of the present invention comprises: a biological signal measurement section configured to measure an electroencephalogram signal of a user; a sound stimulation output section configured to present a sound stimulation group to the user, the sound stimulation group including a first sound, a second sound, and a third sound which are pure tones of a same frequency and which consecutively decrease in sound pressure within a predetermined range; an extraction section configured to extract, from the electroencephalogram signal in a predetermined zone defined based on a point of presenting at least one of the second sound and the third sound as a starting point, an N1-P2-amplitude related or wavelet-coefficient related characteristic amount of event-related potential of the electroencephalogram signal; and a determination section configured to determine an uncomfortable sound pressure at the frequency of the sound stimulation group based on the characteristic amount extracted by the extraction section.

In one embodiment, the determination section determines the uncomfortable sound pressure by referring to a predetermined criterion which previously defines association between characteristic amounts and uncomfortable sound pressure values.

In one embodiment, the uncomfortable sound pressure estimation system further comprises: a sound stimulation group determination section configured to determine the frequency of the sound stimulation group; and a sound pressure determination section configured to determine sound pressures of the first sound, the second sound, and the third sound so as to consecutively decrease within the predetermined range, wherein, the sound stimulation output section outputs the first sound, the second sound, and the third sound at the frequency determined by the sound stimulation group determination section and at the sound pressures determined by the sound pressure determination section.

In one embodiment, the sound pressure determination section determines the sound pressures of the sound stimulation group to be sound pressures which are lower than a predetermined threshold value.

In one embodiment, the sound pressure determination section determines the sound pressures of the sound stimulation group to be sound pressures higher than a hearing threshold level of the user.

In one embodiment, the sound stimulation output section outputs the sound stimulation group so that the first sound, the second sound, and the third sound decrease by every 5 dB or decrease by every 10 dB.

In one embodiment, the determination section retains a predetermined criterion which previously defines association between N1-P2 amplitude or wavelet characteristic amounts and uncomfortable sound pressure values, and determines the uncomfortable sound pressure by making a linear discrimination using the characteristic amount extracted by the extraction section and the predetermined criterion.

In one embodiment, when the determination section retains a predetermined criterion which defines association between N1-P2 amplitudes and uncomfortable sound pressure values, the extraction section extracts an N1-P2-amplitude related characteristic amount of event-related potential of the electroencephalogram signal; and when the determination section retains a predetermined criterion which previously defines association between wavelet characteristic amounts and uncomfortable sound pressure values, the extraction section extracts a wavelet-coefficient related characteristic amount.

In one embodiment, the determination section retains the predetermined criterion for each of a right or left ear and for each frequency, and switches the criterion to be used depending on the right or left ear and frequency of the sound stimulation group.

In one embodiment, the extraction section calculates a wavelet coefficient of an electroencephalogram signal in a zone defined as a point of time of 350 ms or less from the point of presenting each of the first sound to the third sound, and defines a value obtained through averaging over a predetermined frequency range and a predetermined time range as a characteristic amount.

In one embodiment, the predetermined frequency range is between 5 Hz and 12.5 Hz.

In one embodiment, the predetermined time range is 50 ms.

In one embodiment, a HTL value defines the smallest sound pressure of a pure tone that allows it to be heard by the user, and the predetermined threshold value is 90 dBHL when the HTL value is 20 dBHL or less; 95 dBHL when the HTL value is 50 dBHL or less; 100 dBHL when the HTL value is 65 dBHL or less; 105 dBHL when the HTL value is 75 dBHL or less; 115 dBHL when the HTL value is 90 dBHL or less; and 120 dBHL when the HTL value is 95 dBHL or more.

In one embodiment, the uncomfortable sound pressure estimation system further comprises an input section to which a hearing threshold level of the user is input.

An uncomfortable sound pressure estimation apparatus according to an embodiment of the present invention comprises: a sound stimulation output section configured to present a sound stimulation group to the user, the sound stimulation group including a first sound, a second sound, and a third sound which are pure tones of a same frequency and which consecutively decrease in sound pressure within a predetermined range; an extraction section configured to extract, in an electroencephalogram signal measured by a biological signal measurement section of the uncomfortable sound pressure estimation system, a characteristic amount concerning event-related potential of the electroencephalogram signal in a predetermined zone defined based on a point of presenting at least one of the second sound and the third sound as a starting point; and a determination section configured to determine an uncomfortable sound pressure at the frequency of the sound stimulation group based on the extracted characteristic amount.

An uncomfortable sound pressure estimation method according to an embodiment of the present invention comprises: measuring an electroencephalogram signal of a user; presenting a sound stimulation group to the user, the sound stimulation group including a first sound, a second sound, and a third sound which are pure tones of a same frequency and which consecutively decrease in sound pressure within a predetermined range; from the electroencephalogram signal in a predetermined zone defined based on a point of presenting at least one of the second sound and the third sound as a starting point, extracting an N1-P2-amplitude related or wavelet-coefficient related characteristic amount of event-related potential of the electroencephalogram signal; and determining an uncomfortable sound pressure at the frequency of the sound stimulation group based on the extracted characteristic amount.

A computer program according to an embodiment of the present invention is a computer program stored on a non-transitory computer-readable medium to be executed by a computer mounted in an uncomfortable sound pressure estimation apparatus of an uncomfortable sound pressure estimation system, wherein the computer program causes the computer to execute: acquiring an electroencephalogram signal of a user; presenting a sound stimulation group to the user, the sound stimulation group including a first sound, a second sound, and a third sound which are pure tones of a same frequency and which consecutively decrease in sound pressure within a predetermined range; from the electroencephalogram signal in a predetermined zone defined based on a point of presenting at least one of the second sound and the third sound as a starting point, extracting an N1-P2-amplitude related or wavelet-coefficient related characteristic amount of event-related potential of the electroencephalogram signal; and determining an uncomfortable sound pressure at the frequency of the sound stimulation group based on the extracted characteristic amount.

Hereinafter, with reference to the attached drawings, embodiments of the uncomfortable sound pressure estimation system according to the present invention will be described.

The uncomfortable sound pressure estimation system according to the present invention is able to estimate an uncomfortable sound pressure by presenting a presented sound whose sound pressure is of a level that is not felt uncomfortable to the user. Prior to describing the estimation technique, experiments conducted by the inventors, and the experimental results thereof, will be described. Characteristics of event-related potential that enable UCL estimation, which have been found by the inventors from experimental data, will be described.

(Description of Experimental Outline)

1. Experimental Outline

The inventors have conducted the following two experiments in order to collect fundamental data for estimating an uncomfortable sound pressure concerning a pure tone, with a view to realizing an uncomfortable sound pressure estimation which objectively measures a UCL in short time and with a high precision.

One is a subjective report experiment of measuring a UCL based on subjective reporting. The subjective report experiment was conducted before and after an electroencephalogram measurement experiment. The UCL data obtained from this subjective report experiment was used as reference data against which any brain-based estimation was to be contrasted.

Another is an electroencephalogram measurement experiment of measuring responses to sound stimulations. In the electroencephalogram measurement experiment, pure tones of the same frequency were presented totaling three times in succession, with monotonously-descending sound pressure changes of every 5 dBHL, and event-related potentials in response to the respective sound stimulations of first to third sounds were measured.

Hereinafter, sound stimulations being presented a plurality of times successively with monotonously-descending sound pressure changes may also be referred to as "decrescendo stimulations". Event-related potentials to such sound stimulations were acquired for use as data in UCL value estimation.

As a result, the inventors have found that a UCL conforming to subjective reporting can be estimated even when decrescendo stimulations are presented at sound pressures lower than a sound pressure which is generally evaluated to be the UCL, by applying linear discrimination to a change pattern of wavelet coefficients calculated through wavelet transform of event-related potentials in response to the first to third sounds.

Herein, it is assumed that a sound pressure lower than a sound pressure which is generally evaluated to be the UCL varies depending on the HTL value. For example, according to works of Pascoe (Pascoe, D. P. (1988). (Clinical measurements of the auditory dynamic range and their relation to formulas for hearing aid gain. In lensen. H. 1. (Ed.) Hearing Aid Fitting: Theoretical and Practical Views 13th Danavox Symposium. Copenhagen: Stougaard.)), a value which is at least 5 dB lower than an estimated UCL value for each HTL value as shown in FIG. 15 may be designated the aforementioned "sound pressure lower than a sound pressure which is generally evaluated to be the UCL".

Note that it is when a sound stimulation has a sound pressure which is higher than the HTL that any event-related potential will be induced in response to that sound stimulation. In other words, a range of sound pressures lower than a sound pressure which is generally evaluated to be the UCL should be a range of sound pressures higher than the HTL. With this technique, a UCL estimation is achieved in a short time and with a high accuracy, without presenting overbearing sounds.

Hereinafter, the experiments conducted by the inventors and the results thereof, and characteristic features of electroencephalograms which have been found through their analysis will be described in detail. Thereafter, as an embodiment of the present disclosure, an outline of the uncomfortable sound pressure estimation system, and its detailed configuration and operation will be described.

(Experimental Conditions)

2. UCL subjective report experiment and electroencephalogram measurement experiment 2-1. UCL Subjective Report Experiment The experimental participants were 15 adults, who were no longer in school, having normal hearing (28 to 49 years old).

The subjective report experiment was conducted before and after the electroencephalogram measurement experiment. Similarly to Non-Patent Document 1, discontinuous sounds were presented by ascending method using an audiometer, and an uncomfortably loud sound pressure was reported by each experimental participant, this sound pressure being defined as the UCL. For each of three frequencies (1000, 2000, 4000 Hz) to be presented in the electroencephalogram measurement experiment, the inventors took measurement for both ears, one ear at a time. In order to prevent the experimental participants from anticipating the sound pressure, the sound pressure at the start of the experiment was randomly selected from among 60, 65, and 70 dB. The sound pressure of the discontinuous sounds ascended by every 5 dB. An uncomfortably loud sound pressure was reported by raising a hand. Immediately after the participant raised a hand, the sound presentation was stopped, and the sound pressure was recorded as a subjective UCL value.

Hereinafter, results of the subjective report experiment will be described.

All participants were people with normal hearing. However, the results of the subjective report experiment greatly differed from individual to individual. For example, for the same frequency, there was a difference of 40 dB at the most.

This indicates that the definition of "unbearably loud" may greatly vary from individual to individual. Thus, it can be said that UCL measurement through subjective reporting is difficult.

FIG. 1 shows UCL measurement results of individuals which were measured through subjective reporting in the subjective report experiment. FIG. 1 indicates average values of two measurement results each. The sound pressure is in units of dBHL. As can be seen from the standard deviation for the right or left ear and for each different frequency shown in FIG. 1, there are some fluctuations in the subjective UCL value. It can be seen that there are large fluctuations among individuals.

2-2. Electroencephalogram Measurement Experiment

In the electroencephalographic experiment, for each of three frequencies (1000 Hz, 2000 Hz, 4000 Hz), sound stimulations were presented at three sound pressures (80, 75, 70 dBHL) lower than a sound pressure which is generally evaluated to be the UCL. The three sound pressures were monotonously descending. Then, a characteristic change in the event-related potential for each sound stimulation was examined. Hereinafter, with reference to FIG. 2, FIG. 3A, FIG. 3B and FIG. 4, the experimental setting and experimental results of the electroencephalogram measurement experiment will be described.

The experimental participants were the same 15 adults in the subjective report experiment, who were no longer in school (28 to 49 years old) and who had normal hearing.

As the sound stimulations, the inventors used toneburst sounds with a duration of 50 ms. Each sound stimulation had a rise (rise) and (fall) of 3 ms each. For each of the three frequencies (1000, 2000, 4000 Hz) and for each of the right or left ear, characteristic amount variation in the event-related potential against changing sound pressure was examined, by using sound stimulations of the three sound pressures (80, 75, 70 dBHL). A group of sound stimulations pertaining to the same frequency will be referred to as an "sound stimulation group".

The sound stimulations contained in the sound stimulation group were with respect to the same ear at predetermined intervals. Each sound stimulation was presented to one ear through headphones.

FIG. 2 schematically shows sound stimulations presented in the electroencephalogram measurement experiment.

The participants were instructed that there was no need to pay attention to the sound stimulations. The interval between sound stimulations within a sound stimulation group of the same frequency (ISI1 in FIG. 2) was fixed at 300 ms. Moreover, the interval between sound stimulation groups (ISI2 in FIG. 2) was randomly decided within a range of 450±100 ms. The sound stimulation group for the right or left ear and for each different frequency was repeated 30 times (totaling in 180 sound stimulation groups).

In order to reduce taming (habituation) of the auditory evoked potential due to successive presentation of the same sound stimulation group, the inventors determined the frequency and the ear for which to present the sound stimulation group under the following constraints.

the frequency is selected to be different from that of an immediately previous sound stimulation group.

the ear to which the sound stimulation group is presented is randomly selected between right or left. However, in order to ensure randomness of stimulations between the right and left ears, not more than four sound stimulation groups are successively presented to either the right or left ear.

Figure 3A:
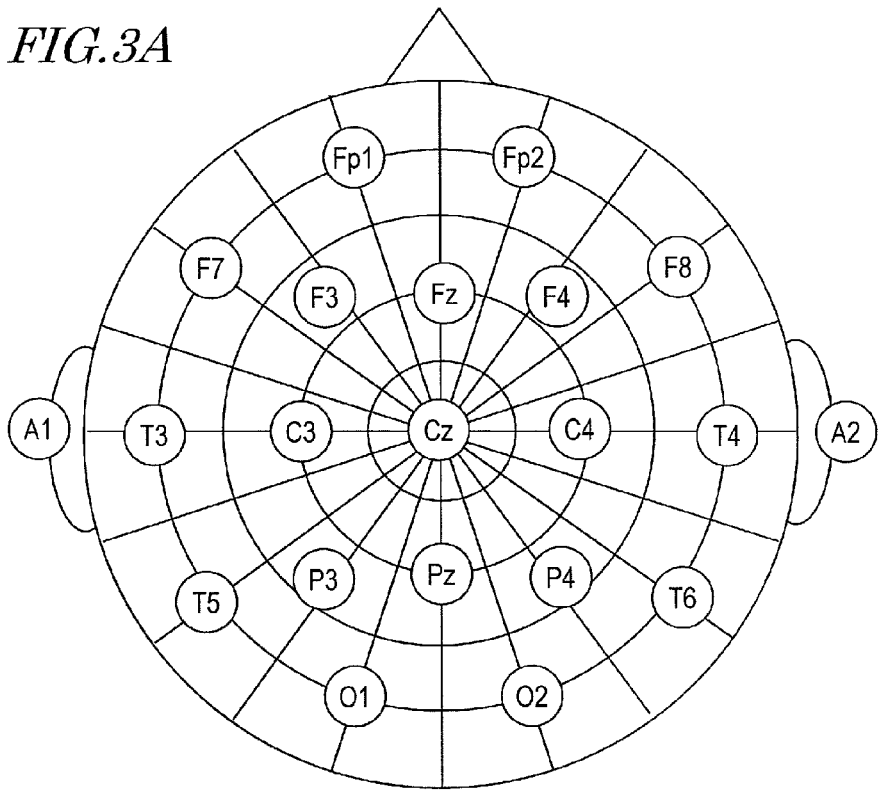
FIGS. 3A and 3B show electrode positions according to the International 10-20 system, and electrode positions in an electroencephalographic experiment conducted by the inventors.
Figure 3B:
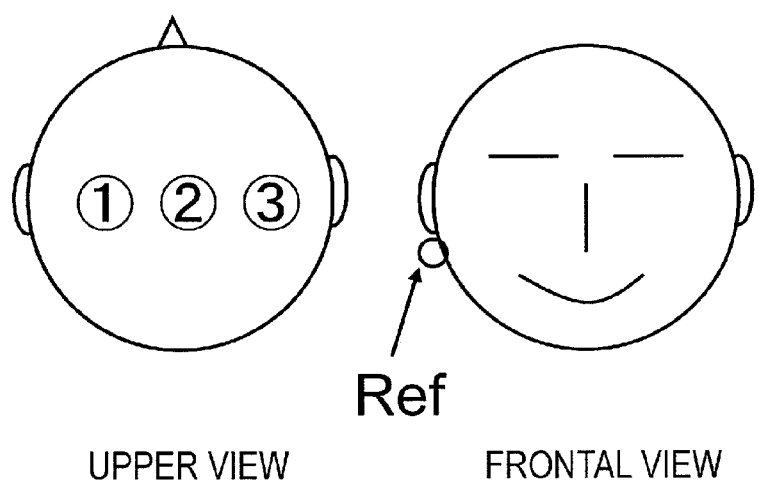

Next, the positions of electrodes to be worn for electroencephalogram measurement will be described. FIG. 3A shows electrode positions according to the International 10-20 system (10-20 System). FIG. 3B shows the positions of electrodes worn in this experiment. In FIG. 3B, circled numbers 1, 2, and 3 represent electrode positions C3, Cz, and C4, respectively. The inventors recorded the electroencephalogram from C3, Cz, and C4 (the International 10-20 system) on the scalp, on the basis of the right mastoid. A "mastoid" is a protrusion of the cranium below the hind root of an ear. FIG. 3B shows the mastoid position as "Ref".

The sampling frequency was 1000 Hz; the time constant was 0.3 seconds; and an analog low-pass filter was applied at 30 Hz. The entire time slot of electroencephalogram data measured off-line was subjected to a 5-20 Hz digital band-pass filter. Thereafter, as an event-related potential in response to a sound stimulation for the right or left ear, for each different frequency, and for each different sound pressure, a waveform from −100 ms to 400 ms was cut out based on the respective sound stimulation as a starting point. As used herein, "−100 ms" means a point in time which is 100 milliseconds before the point in time at which a sound stimulation is presented.

Moreover, for each sound stimulation, an electroencephalogram waveform in a range from 0 ms to 300 ms of the event-related potential was subjected to a continuous wavelet transform to derive a wavelet coefficient for each time and each frequency. As a mother wavelet, the Mexican hat function ($\phi(t)=(1t^2)\exp(t^2/2)$) was used.

The waveforms and wavelet coefficients of event-related potential were arithmetic-meaned, for each individual person, each of the right or left ear, each frequency, and every sound stimulations of first to third sounds. These will be referred to as, respectively, the arithmetic mean waveform and the arithmetic mean wavelet coefficient. Those trials which exhibited an amplitude in absolute value of 50 μV or more at any electrode were excluded from the total arithmetic mean and arithmetic mean, because they presumably are under the influence of noises, e.g., eye movements and blinks.

Then, as a characteristic amount of the event-related potential potentially serving as an index of uncomfortable sound pressure, average values of the arithmetic mean wavelet coefficients over a frequency range from 5 Hz to 12.5 Hz were calculated in every time range of 50 ms (hereinafter referred to as wavelet characteristic amounts).

2-3. Results

Hereinafter, results of the electroencephalogram measurement experiment will be described.

First, in order to confirm that an index of uncomfortable sound pressure estimation exists in the event-related potential against changing sound pressure, arithmetic-meaned event-related potentials were compared on the basis of the subjective UCL value. In order to estimate an uncomfortable sound pressure based on event-related potential, a difference in event-related potential needs to exist that reflects a subjective UCL value of each participant.

Now, as discussed above, the subjective UCL value can only be an index that is prone to fluctuations among participants, because of different personalities existing with respect to overbearing sounds. This makes it difficult to identify the presence or absence of a characteristic amount that reflects a subjective UCL value from the data of each individual person. Therefore, in order to reduce such fluctuations, event-related potentials were arithmetic-meaned and compared while making a distinction between large subjective UCL values and small subjective UCL values. Specifically, an arithmetic mean was taken with respect to the cases where the subjective UCL value for each participant and for each frequency was greater than 95 dBHL, or the cases where it was equal to or less than 95 dBHL, and these results were compared. Note that 95 dBHL is a value near the center of the subjective UCL values of all participants obtained from the subjective report experiment, and there were substantially the same number of cases where the subjective UCL value was greater than 95 dBHL as the cases where it was equal to or less than 95 dBHL.

Figure 4:
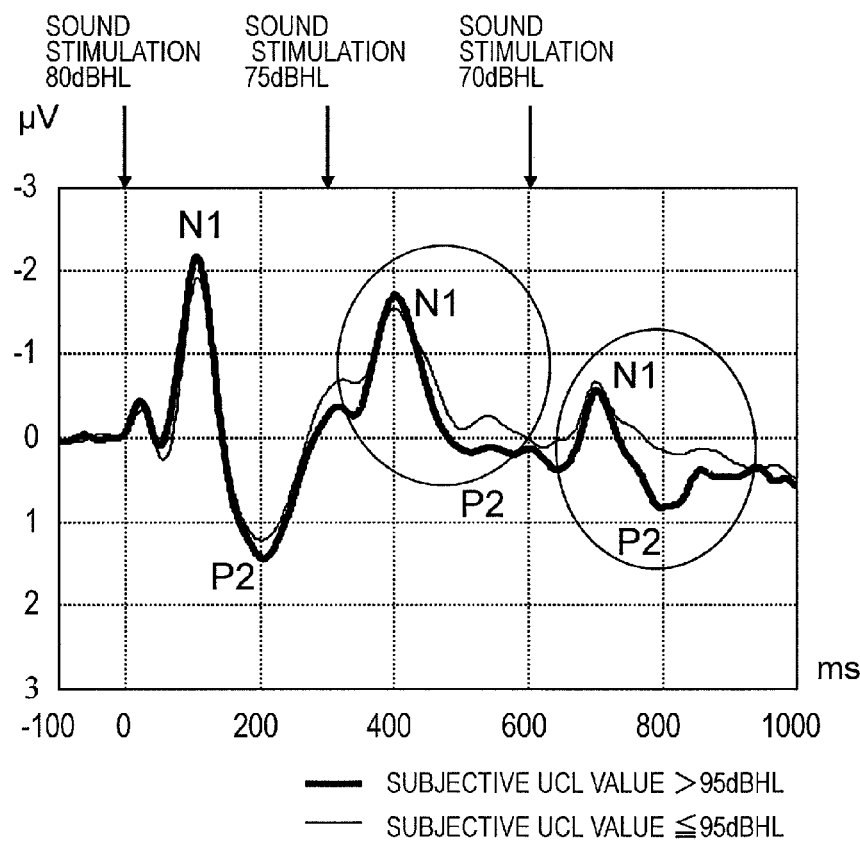
FIG. 4 shows characteristic data of event-related potential in an electroencephalographic experiment conducted by the inventors.

FIG. 4 shows total arithmetic mean electroencephalogram waveforms for different subjective UCL values. Each electroencephalogram waveform subjected to the total arithmetic mean was measured at the central portion (Cz), from 100 ms before the first sound in the sound stimulation group until 400 ms after the third sound. A thick line indicates the case where the subjective UCL value is greater than 95 dBHL, whereas a thin line indicates the case where the subjective UCL value is 95 dBHL or less. The horizontal axis represents time in units of ms, and the vertical axis represents potential in units of μV. On the horizontal axis, 0 ms denotes a point at which the first sound is presented.

It can be seen that, as reckoned from each timing of sound stimulation presentation indicated by an arrow, a negative N1 component is induced at about 100 ms and a positive P2 component is induced at about 200 ms. It can also be seen that there is a difference in the event-related potential at the second sound presentation and thereafter, depending on whether the subjective UCL value is high or low. Specifically, the N1-P2 amplitude is larger in the case where the subjective UCL value is greater than 95 dBHL (indicated by the thick line), than in the case where the subjective UCL value is 95 dBHL or less. This suggests an ability to estimate a UCL based on an index which is the difference in event-related potential at the second sound and thereafter.

Note that an N1-P2 amplitude represents the absolute value of a difference between the negative amplitude of an N1 component and the positive amplitude of a P2 component.

Figure 16:
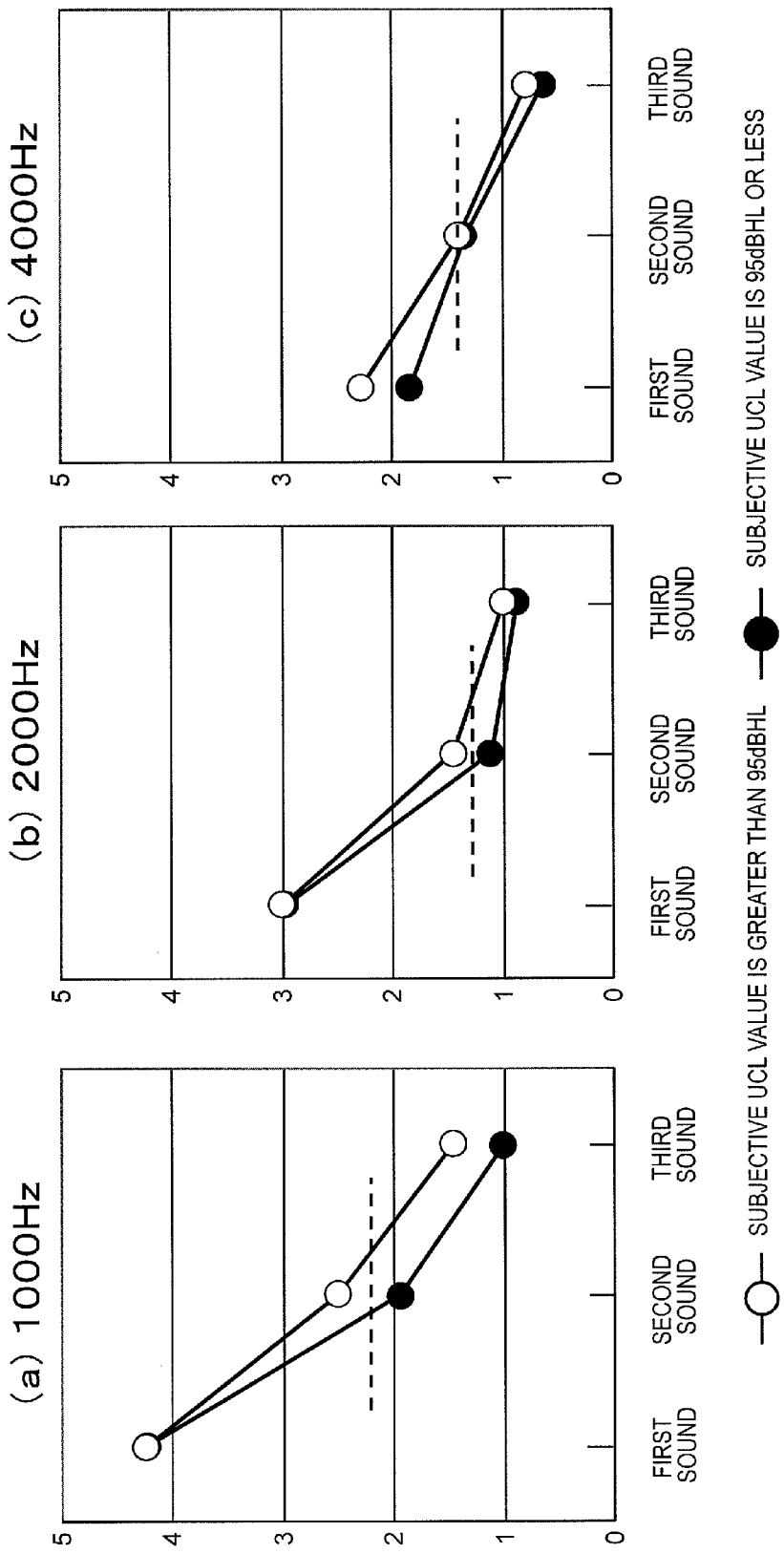
FIG. 16 shows N1-P2 amplitude in response to first to third sounds, with respect to different frequencies.

FIG. 16 shows a relationship between greater or smaller subjective UCL values and the N1-P2 amplitude. For each different frequency, FIG. 16 shows N1-P2 amplitude in response to the first to third sounds, with respect to the case where the subjective UCL value is greater than 95 dBHL and the case where the subjective UCL value is 95 dBHL or less. The N1-P2 amplitude is defined as the absolute value of a difference between an N1 amplitude and a P2 amplitude.

The N1 amplitude is a zone average potential from 90 ms to 110 ms after the presentation of each sound stimulation of the first to third sounds. Similarly, the P2 amplitude is a zone average potential from 190 ms to 210 ms after each sound stimulation presentation.

In the case where the subjective UCL value is greater than 95 dBHL, the N1-P2 amplitude in response to the first to third sounds is 4.24 μV, 2.51 μV, 1.45 μV at 1000 Hz, respectively. Also, the N1-P2 amplitude is 2.99 μV, 1.45 μV, and 1.00 μV at 2000 Hz. Also, the N1-P2 amplitude is 2.28 μV, 1.40 μV, and 0.78 μV at 4000 Hz.

In the case where the subjective UCL value is 95 dBHL or less, the N1-P2 amplitude in response to the first to third sounds is 4.24 μV, 1.95 μV, 0.99 μV at 1000 Hz; 2.95 μV, 1.11 μV, 0.88 μV at 2000 Hz; and 1.84 μV, 1.33 μV, 0.63 μV at 4000 Hz. At any frequency, the N1-P2 amplitude in response to the second and third sounds is larger in the case where the subjective UCL value is greater than 95 dBHL than in the case where the subjective UCL value is 95 dBHL or less. This indicates that, depending on the subjective UCL value, the event-related potential for changing sound pressure varies at least in terms of N1-P2 amplitude.

Next, the inventors examined the relationship between the subjective UCL value and the wavelet characteristic amount. Then, the inventors conducted a discriminant analysis in order to ascertain the accuracy of an uncomfortable sound pressure estimation using changes in this characteristic amount.

Figure 5:
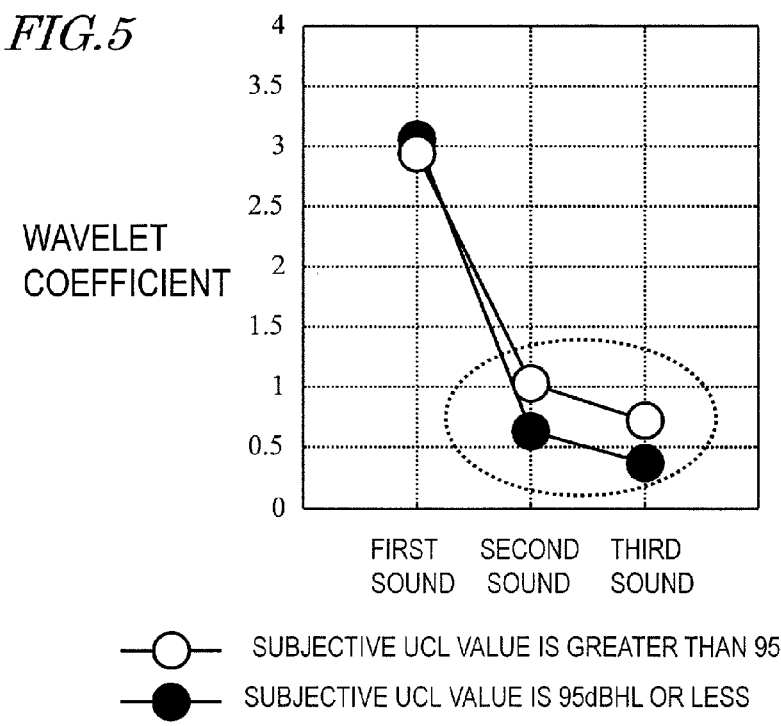
FIG. 5 shows examples of wavelet coefficients of event-related potentials in an electroencephalographic experiment conducted by the inventors.

FIG. 5 shows wavelet characteristic amounts in response to the first to third sounds, under different conditions and different subjective UCL values. As exemplary results, FIG. 5 indicates wavelet characteristic amounts in a time slot from 201 ms to 250 ms, this time slot defining a time zone as reckoned from a point at which each sound stimulation is presented. It can be seen that, although the difference in wavelet characteristic amount is small with respect to the first sound (80 dBHL), the wavelet characteristic amounts in response to the second sound (75 dBHL) and the third sound (70 dBHL) differ depending on the subjective UCL value. Specifically, the wavelet characteristic amount in response to the second and third sounds are larger in the case where the subjective UCL value is greater than 95 dBHL, than in the case where the subjective UCL value is 95 dBHL or less. This indicates that, depending on the subjective UCL value, the event-related potential for changing sound pressure varies in terms of wavelet characteristic amount.

In order to ascertain the accuracy of an uncomfortable sound pressure estimation using characteristic amount variation in the event-related potential, the inventors have conducted a discriminant analysis. Linear discrimination was used as the technique of discriminant analysis, which was conducted by allowing the subjective UCL value for each of the right or left ear and for each frequency obtained through the aforementioned subjective report experiment to be trained with a wavelet characteristic amount of an event-related potential for each sound pressure. In order to find characteristic amounts that are suitable for UCL estimation, the error of each characteristic amount (alone or in combination with any other(s)) with respect to the subjective UCL value was ascertained, and a comparison was made between errors resulting from different numbers of characteristic amounts used in combination.

Hereinafter, the data to be used in linear discrimination, and the linear discrimination process conducted will be described. FIG. 6 shows an example of data used in an uncomfortable sound pressure estimation. Each subjective UCL value shown in FIG. 6 was measured through the subjective report experiment for each participant, each of the right or left ear, and each frequency. In FIG. 6, the columns corresponding to the first to third sounds show wavelet characteristic amounts (at 201 ms to 250 ms after sound stimulation) of the event-related potentials in response to the first to third sounds of a sound stimulation group. These characteristic amounts for each sound stimulation group were trained against the respective subjective UCL value, and a linear discrimination was conducted.

The inventors conducted the linear discrimination by using target data against training data, the target data for linear discrimination being the characteristic amounts of the event-related potentials for the sound stimulation group taken for a given participant, and the training data having been generated from the characteristic amounts of event-related potentials of other people. Moreover, the inventors generated the training data from the characteristic amounts of the event-related potentials of other people for each condition, each of the right or left ear, and each frequency.

For example, if the target data for linear discrimination was that of participant 01 for the right ear and 1000 Hz, the training data was generated from the characteristic amounts of the data of the event-related potential for the right ear and 1000 Hz from a participant other than participant 01. As the characteristic amounts, the aforementioned wavelet characteristic amounts (time range 50 ms) were used.

In order to explore the possibility of uncomfortableness sound pressure estimation, in the case where a plurality of characteristic amounts were to be employed in combination, characteristic amounts were added in extra columns, in either the target data for linear discrimination or the training data. For example, if wavelet characteristic amounts from 151 ms to 200 ms and wavelet characteristic amounts from 201 ms to 250 ms were to be employed in combination, in addition to the first to third columns being allocated to the characteristic amounts in response to the first to third sounds regarding the former, fourth to sixth columns were allocated to the characteristic amounts in response to the first to third sounds regarding the latter. An "estimation error" was defined as the absolute value of a difference between a subjective UCL value and a result of uncomfortable sound pressure estimation. Accuracy of estimation was measured on the basis of an average estimation error, which was obtained by averaging the estimation errors of all participants with respect to right and left and all frequencies.

Figure 7:
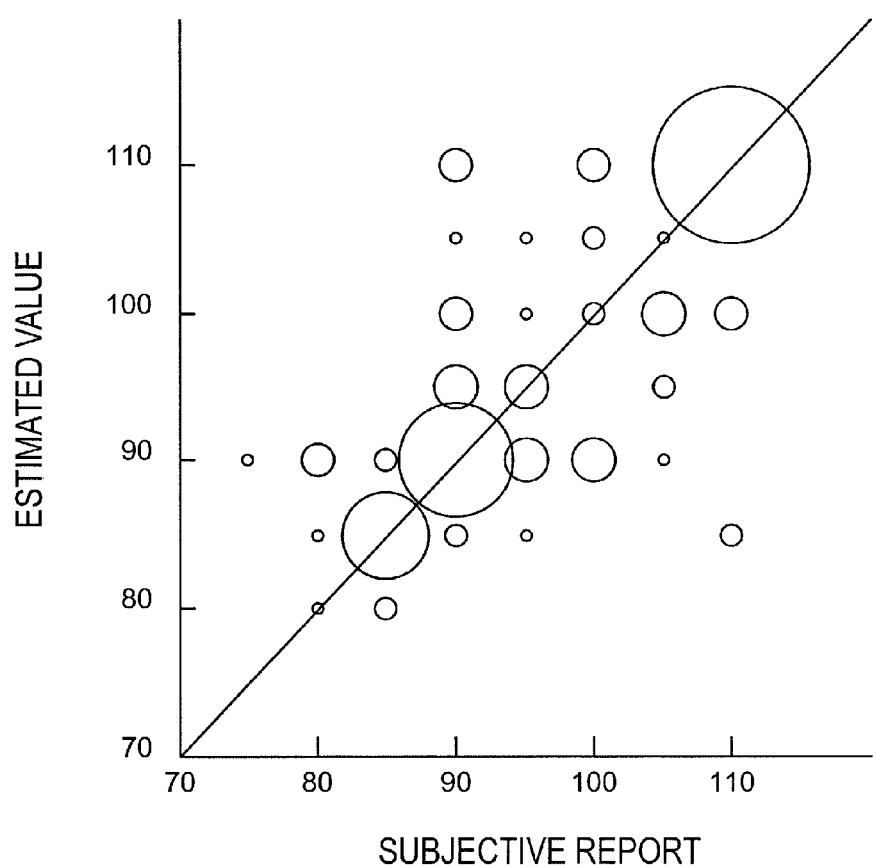
FIG. 7 shows fluctuations between subjectively-reported values obtained from a subjective report experiment and results of uncomfortable sound pressure estimation estimated from an electroencephalographic experiment.

FIG. 7 shows, as exemplification of linear discrimination results, distributions under different conditions of results of uncomfortable sound pressure estimation based on subjective UCL values and linear discrimination, in the case where five characteristic amounts are used in combination. The analysis was conducted for each condition, each of the right or left ear, and each frequency; however, FIG. 7 shows altogether the results obtained for each of the right or left ear and for each frequency. As indicated by the scale in FIG. 7, the horizontal axis represents subjective UCL values in units of dBHL, and the vertical axis represents uncomfortable sound pressure estimation values in units of dBHL. Results of uncomfortable sound pressure estimation with respect to subjective UCL values are indicated by ○ symbols as lattice points. The size of any ○ symbol reflects the frequency distribution of the particular estimation result. The average estimation error was 5.2 dB. From these results, it can be seen that uncomfortable sound pressures which are correlated with the subjective UCL values have successfully been estimated, although there are some fluctuations.

Note that a discriminant analysis may be made not only with wavelet characteristic amounts, but also with P1-N1 amplitude or N1-P2 amplitude information. Note that training data may be generated irrespective of the right or left ear and irrespective of sound frequency.

Thus, it has been made clear through the subjective report experiment and electroencephalogram measurement experiment conduced by the inventors that, when pure tones of the same frequency are presented totaling three times in succession at monotonously-descending sound pressure changes within a range of sound pressures lower than a sound pressure which is generally evaluated to be the UCL, it is possible to estimate an uncomfortable sound pressure by using characteristic amounts concerning the wavelet coefficients of electroencephalograms in response to the respective sound stimulations of first to third sounds.

Embodiment 1

Hereinafter, an uncomfortable sound pressure estimation system will be described in outline first. Thereafter, the construction and operation of an uncomfortable sound pressure estimation system including the uncomfortable sound pressure estimation apparatus will be described.

An uncomfortable sound pressure estimation system according to the present embodiment presents pure tones of the same frequency three times in succession at monotonously descending sound pressures, in a sound pressure range higher than the HTL and lower than a sound pressure which is generally evaluated to be the UCL, extracts electroencephalographic characteristic amounts in response to the respective sound stimulations of the first to third sounds, and measures an uncomfortable sound pressure from a change pattern of the characteristic amounts.

In the present embodiment, by providing a probe electrode at the central portion (Cz) and a reference electrode at the right mastoid, an electroencephalogram is measured as a potential difference between the probe electrode and the reference electrode. Note that the level and polarity of a-characteristic component of the event-related potential may possibly vary depending on the sites at which electrodes for electroencephalogram measurement are worn, and on the positions at which the reference electrode and the probe electrode are set. However, based on the following description, those skilled in the art should be able to extract a characteristic feature of the event-related potential and perform an uncomfortable sound pressure measurement by making appropriate modifications in accordance with the particular reference electrode and probe electrode used. Such variants are encompassed within the present disclosure.

<Environment of Use>

Figure 8:
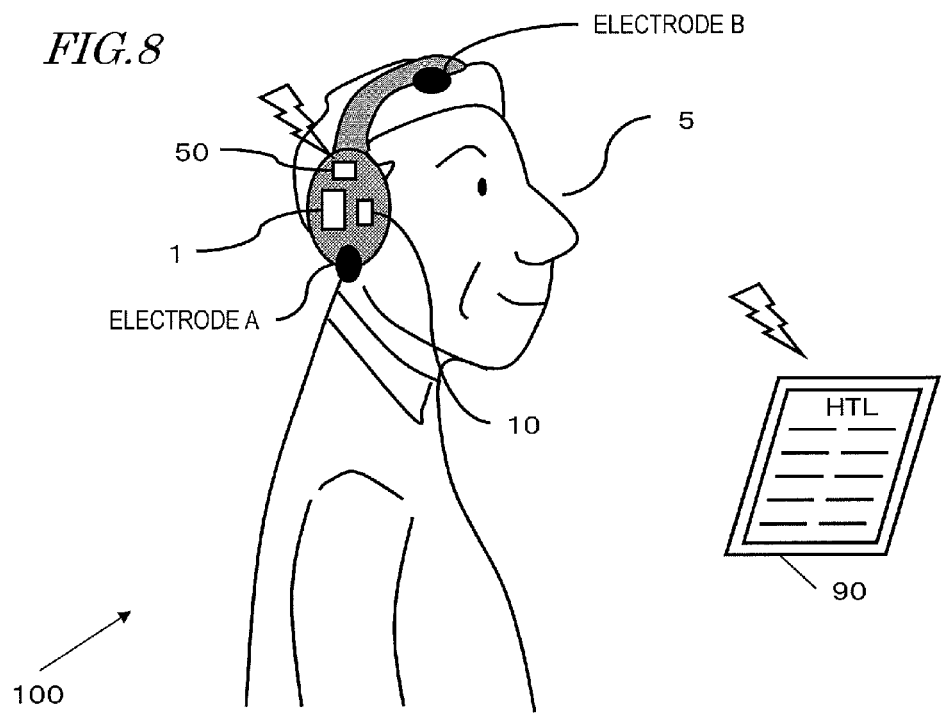
FIG. 8 shows an environment of use for an uncomfortable sound pressure estimation system.

FIG. 8 shows a construction and an environment of use for an uncomfortable sound pressure estimation system 100 according to the present embodiment. The uncomfortable sound pressure estimation system 100 (hereinafter referred to as the "estimation system 100") corresponds to the system construction of Embodiment 1 described later and shown in FIG. 10.

The estimation system 100 includes an uncomfortable sound pressure estimation apparatus 1, a sound stimulation output section 10, a biological signal measurement section 50, and an HTL input section 90.

The sound stimulation output section 10 is headphones or loudspeakers for outputting a sound stimulation to the user 5, for example.

The biological signal measurement section 50 is a measuring instrument which measures a biological signal of the user. In the present disclosure, one example of the biological signal measurement section 50 may be an electroencephalograph. The biological signal measurement section 50 is connected to at least two electrodes A and B. For example, electrode A is attached to a mastoid of the user 5, whereas electrode B is attached to a central portion (so-called Cz) on the scalp of the user 5. The biological signal measurement section 50 measures an electroencephalogram of the user 5 that corresponds to a potential difference between electrode A and electrode B, and outputs an electroencephalogram signal.

The HTL input section 90 is an input device which accepts an HTL value of each user, which is measured in advance. The HTL input section 90 receives an input of an HTL value for the right or left and for each frequency from the user or an evaluator. The input HTL value is sent to the uncomfortable sound pressure estimation apparatus 1. FIG. 8 shows an example where the HTL input section 90 is provided separately from the uncomfortable sound pressure estimation apparatus 1.

The HTL input section 90 may be e.g. a tablet terminal, so long as it is capable of accepting an HTL value input. In that case, it is connected in a wired or wireless manner to the uncomfortable sound pressure estimation apparatus 1 to perform exchange of the input HTL value. Moreover, the HTL input section 90 may be provided within a pair of headphones in which the uncomfortable sound pressure estimation apparatus 1 is incorporated.

In a sound pressure range higher than the HTL and lower than a sound pressure which is generally evaluated to be the UCL, the estimation system 100 determines a sound stimulation group (a first sound to a third sound) of a certain frequency, at monotonously descending sound pressures. Then, as characteristic amounts, the estimation system 100 extracts wavelet coefficients of the electroencephalogram (event-related potential) of the user 5 measured based on the points of presenting the first sound to the third sound as starting points. Then, from a change pattern of the characteristic amounts in response to the first sound to the third sound, the estimation system 100 estimates an uncomfortable sound pressure for that user. The details of the respective component elements and processes will be described later.

In the housing of the uncomfortable sound pressure estimation apparatus 1 (hereinafter referred to as the "estimation apparatus 1") shown in FIG. 8, the biological signal measurement section 50 and the sound stimulation output section 10 are provided. However, the biological signal measurement section 50 and the sound stimulation output section 10 of the uncomfortable sound pressure estimation apparatus 1 may be provided in a separate housing. In that case, an electroencephalogram signal measured by the biological signal measurement section 50 is sent to the uncomfortable sound pressure estimation apparatus 1, which is connected in a wireless or wired manner.

The uncomfortable sound pressure estimation apparatus 1 determines the right or left ear, frequency, sound pressure, and timing for the sound stimulations for uncomfortable sound pressure estimation. Generating the determined sound stimulations, the sound stimulation output section 10 presents the sound stimulations determined by the uncomfortable sound pressure estimation apparatus 1 to the user 5.

Moreover, from event-related potentials which are cut out based on the sound stimulations of the first sound to the third sound as starting points, it extracts characteristic amounts for estimating the uncomfortable sound pressure, and based on the pattern of characteristic amount variation against changing sound pressure, determines an uncomfortable sound pressure for each of the right or left ear and for each different frequency.

<Hardware Construction of the Uncomfortable Sound Pressure Estimation Apparatus 1>

Figure 9:
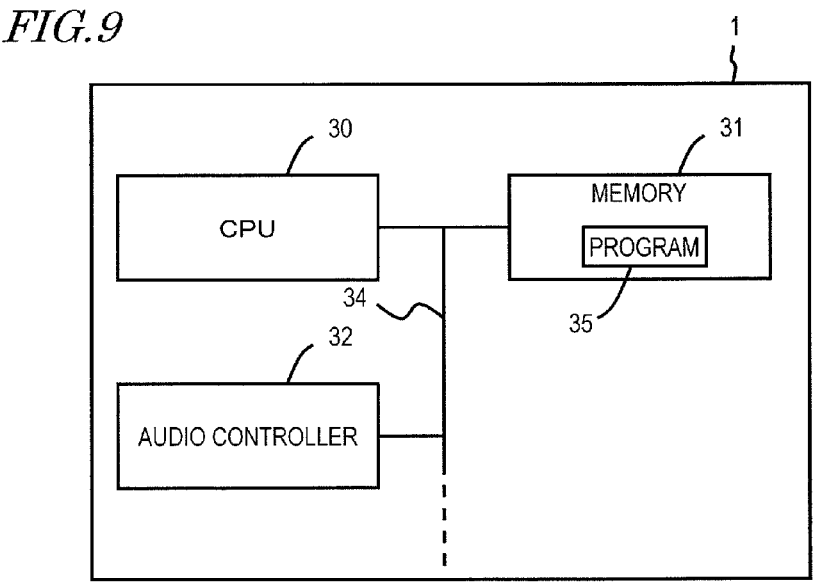
FIG. 9 shows a hardware construction according to Embodiment 1.

FIG. 9 shows the hardware construction of the uncomfortable sound pressure estimation apparatus 1 according to the present embodiment. The uncomfortable sound pressure estimation apparatus 1 includes a CPU 30, a memory 31, and an audio controller 32. The CPU 30, the memory 31, and the audio controller 32, are interconnected via a bus 34, so that data exchange among them is possible.

The CPU 30 executes a computer program 35 which is stored in the memory 31. A processing procedure as illustrated by a subsequently-described flowchart is described in the computer program 35. In accordance with the computer program 35, the uncomfortable sound pressure estimation apparatus 1 performs processes of controlling the entire estimation system 100, such as generation of sound stimulations, extraction of characteristic amounts of event-related potentials, and discriminant analysis for uncomfortable sound pressure determination. These processes will be described in detail later.

In accordance with instructions from the CPU 30, the audio controller 32 outputs the sound stimulations for presentation via the sound stimulation output section 10 at designated sound pressures.

Note that the uncomfortable sound pressure estimation apparatus 1 may be implemented as a piece of hardware (e.g., a DSP) consisting of a semiconductor circuit having a computer program incorporated therein. Such a DSP can realize all functions of the aforementioned CPU 30, memory 31, and audio controller 32 on a single integrated circuit.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 9 (e.g., a PC) is able to function as the uncomfortable sound pressure estimation apparatus 1 according to the present embodiment.

Figure 10:
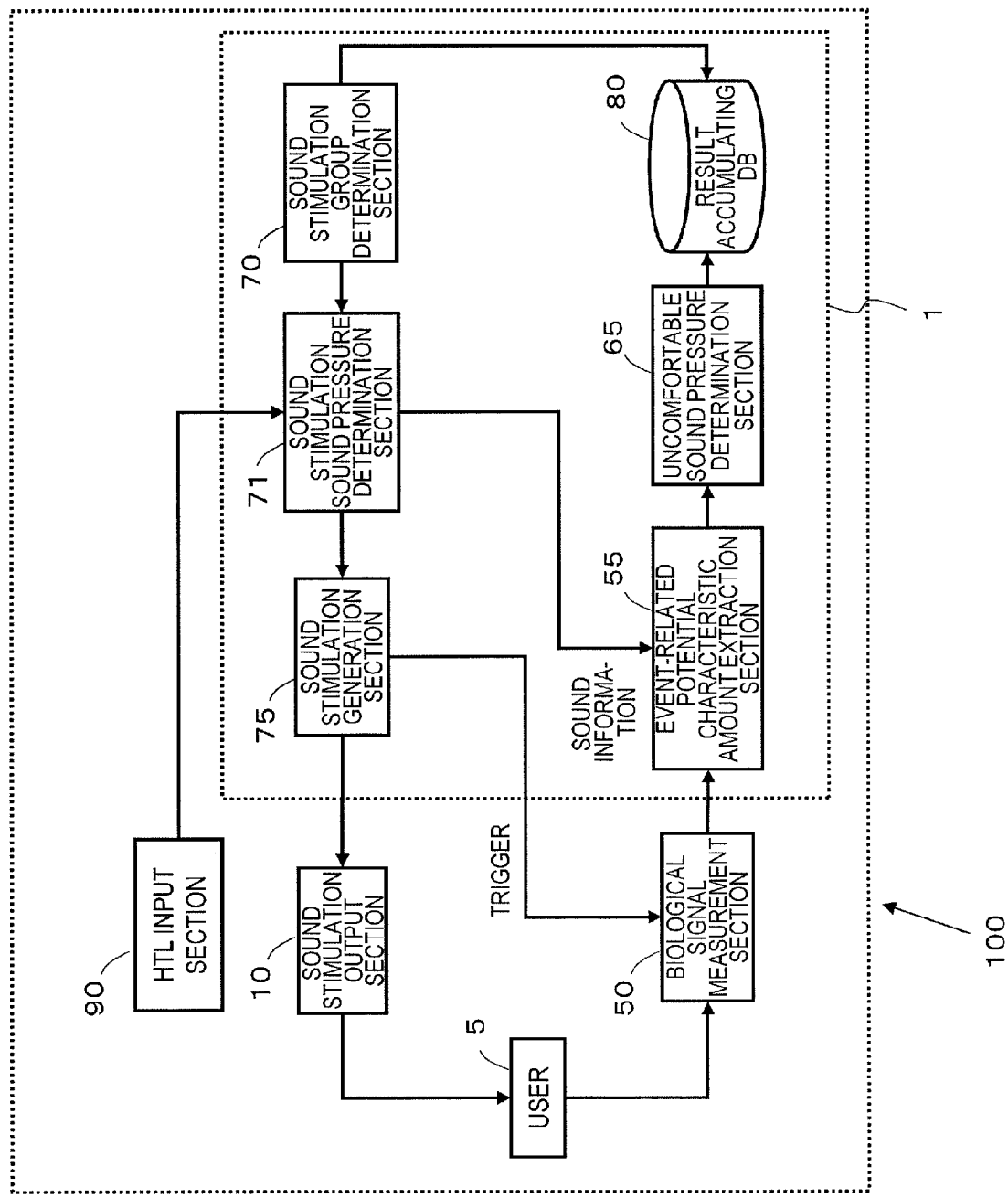
FIG. 10 shows the functional block construction of an uncomfortable sound pressure measurement system according to Embodiment 1.

FIG. 10 shows the functional block construction of the estimation system 100 according to the present embodiment. The estimation system 100 includes the sound stimulation output section 10, the biological signal measurement section 50, the HTL input section 90, and the uncomfortable sound pressure estimation apparatus 1. The component elements of the estimation system 100 are connected in a wired or wireless manner. For example, the estimation apparatus 1 is connected to the sound stimulation output section 10 and the biological signal measurement section 50 in a wired or wireless manner. The user 5 block is illustrated for ease of explanation.

The uncomfortable sound pressure estimation apparatus includes an event-related potential characteristic amount extraction section 55, an uncomfortable sound pressure determination section 65, a sound stimulation group determination section 70, a sound stimulation sound pressure determination section 71, a sound stimulation generation section 75, and a result accumulating DB 80. Hereinafter, the event-related potential characteristic amount extraction section will be referred to as the "extraction section", the uncomfortable sound pressure determination section as the "determination section", and the sound stimulation sound pressure determination section as the "sound pressure determination section".

In FIGS. 8 and 10, the uncomfortable sound pressure estimation apparatus 1 does not include the sound stimulation output section 10. However, this construction is an example. For example, an uncomfortable sound pressure estimation apparatus 1 which at least includes the sound stimulation output section 10, the extraction section 55, and the determination section 65 may be provided. These component elements can be accommodated in a single housing to be operated as a single uncomfortable sound pressure estimation apparatus.

The respective functional blocks of the uncomfortable sound pressure estimation apparatus 1 correspond to functions which are realized by the CPU 30, the memory 31, and the audio controller 32 as a whole upon executing the program which has been described in conjunction with FIG. 9.

Hereinafter, the respective component elements of the estimation system 100 will be described.

The HTL input section 90 accepts input of an HTL value for each of the right or left ear and for each frequency of the user. Examples of HTL values to be input to the HTL input section 90 are shown in FIG. 11. FIG. 11 shows HTL values from 250 Hz to 4000 Hz for each of the right or left ear, as measured by an audiometer. The HTL values may be in units of dBHL, thus conforming to the audiometer, for example. The HTL input section 90 sends the input HTL value to the estimation apparatus 1. In the case where measurement is to be taken for only one ear, the HTL input section 90 may accept input of data for only either HTL value, and send it.

<Sound Stimulation Group Determination Section 70>

The sound stimulation group determination section determines information of a plurality of sound stimulations to be presented to the user 5. The information of the sound stimulation group contains the ear to which the sound stimulations are to be presented (the right ear or the left ear), the frequencies of the sound stimulations to be presented, the duration of the sound stimulations within the sound stimulation group, and the interval between the plurality of sound stimulations.

The sound stimulation group determination section 70 may randomly decide the frequency and the ear for which to present the sound stimulation under the following constraints, for example.

No sound stimulation of the same frequency as that of an immediately previous sound stimulation group is selected.

The ear is preferably selected in random order between right and left; however, it is preferable that not more than four sound stimulation groups are successively presented to either the right or left ear.

In accordance with the above, the influence of taming (habituation) of the electroencephalogram due to successive presentation of sound stimulation groups to the same ear and with the same frequency is reduced, whereby uncomfortable sound pressure estimation can be realized with a high precision. The duration of a sound stimulation may be set to e.g. 25 ms or more, so that an auditory evoked potential will be stable induced. Moreover, the interval between stimulations is set to a time which is equal to or greater than the duration of a sound stimulation but equal to or less than 1 second. For example, it may be 300 ms, or 200 ms.

<Sound Stimulation Sound Pressure Determination Section 71 (Sound Pressure Determination Section 71)>

From the sound stimulation group determination section 70, the sound pressure determination section 71 receives the information of the ear to which the sound stimulation group is presented (the right ear or the left ear), frequency, duration of each sound stimulation in the sound stimulation group, and interval between stimulations. Moreover, from the HTL input section 90, the sound pressure determination section 71 receives the HTL value information for each of the right or left ear and for each frequency. The first sound, the second sound, and the third sound at least has the same frequency. It is meant that "same frequency" is inclusive of sounds having a difference in frequency that is smaller than humans can aurally distinguish. In the present specification, a difference of 5 Hz or less, for example, is regarded as pertaining to the same frequency.

The sound pressure determination section 71 determines the sound pressures of the first sound to the third sound in the sound stimulation group within a sound pressure range which is higher than the HTL value received from the HTL input section 90 and lower than a predetermined threshold value. The values of sound pressure of the first sound to the third sound are determined so that their sound pressures decrease consecutively. Herein, the "predetermined threshold value" is a sound pressure which is generally evaluated to be the UCL, for example. In other words, the sound pressures of the first sound to the third sound are to be determined within a sound pressure range which permits comfortable hearing by the user 5. The sound pressure determination section 71 retains the predetermined threshold value in advance.

For example, consider a case where the HTL value at a given frequency is 50 dBHL, and the predetermined sound pressure is 90 dBHL. In this case, the sound pressure determination section 71 may determine the sound pressure of the first sound to be 80 dBHL, the sound pressure of the second sound to be 75 dBHL, and the sound pressure of the third sound to be 70 dBHL.

Moreover, the sound pressure determination section may be arranged so as to never determine the sound pressure to be greater than the predetermined threshold value. For example, it may be prearranged that the range sound of pressure that can be chosen by the sound pressure determination section 71 is equal to or less than the predetermined threshold value.

<Sound Stimulation Generation Section 75>

Based on the information of the ear to which the sound stimulation group is presented, frequency, duration of each sound stimulation in the sound stimulation group, interval between stimulations, and sound pressure which is received from the sound pressure determination section 71, the sound stimulation generation section 75 generates sound stimulation data or audio signals. Each sound stimulation may be a tone burst sound with a rise and fall of 3 ms, for example.

The sound stimulation generation section 75 sends the sound stimulation group to the sound stimulation output section 10 with a predetermined interval between stimulations, and outputs sound stimulations to the user via the sound stimulation output section 10. At this timing, the sound stimulation generation section 75 outputs a trigger signal(s) to the biological signal measurement section 50. Note that, without outputting any trigger signal, the sound stimulation generation section 75 may only send the generated sound stimulation data to the sound stimulation output section 10.

The sound stimulation data may be generated in such a manner that a single piece of sound stimulation data is created for one sound stimulation group, from which a plurality of sound stimulations that undergo changes in sound pressure at a predetermined time interval are derived, for example. In that case, the trigger signal to be sent to the biological signal measurement section 50 may only be sent at the timing of presenting the first sound.

Note that the sound stimulation generation section 75 may be composed of an input section. Information which is input via the input section by the user 5 or a person who tests the hearing of the user 5 may be utilized as the auditory stimulation information. In other words, in the estimation system 200, auditory stimulations may be externally received, rather than being internally generated.

<Sound Stimulation Output Section 10>

The sound stimulation output section 10 is connected to the sound stimulation generation section 75 in a wired or wireless manner. The sound stimulation output section 10 reproduces sound stimulation data which is generated by the sound stimulation generation section 75, and presents it to the user 5. Preferably, the sound stimulation output section 10 correctly outputs the sound stimulation generated by the sound stimulation generation section 75 to each of the right or left ear. For example, it may be headphones whose frequency characteristics are free of distortion. The sound stimulation output section 10 will also be referred to as the output section. With the sound stimulation to the user 5 as a trigger, the sound stimulation output section 10 may send information of the point at which the sound stimulation was presented, to the extraction section 55.

<Biological Signal Measurement Section 50>

The biological signal measurement section 50 measures a biological signal of the user 5. The user 5 is at least wearing a probe electrode and a reference electrode. As the biological signal, the biological signal measurement section 50 measures an electroencephalogram signal which corresponds to a potential difference between the probe electrode and the reference electrode. Frequency filtering with an appropriate cutoff frequency may be applied to the electroencephalogram signal. Then, an event-related potential may be cut out from the electroencephalogram signal which has been subjected to frequency filtering. The biological signal measurement section 50 sends the measured electroencephalogram or filtered electroencephalogram signal to the extraction section 55. Hereinafter, the measured electroencephalogram signal or filtered electroencephalogram signal may also be referred to as electroencephalogram data.

For example, the biological signal measurement section 50 applies frequency filtering with an appropriate cutoff frequency to the electroencephalogram data, and based on the trigger received from the sound stimulation generation section 75 as a starting point, cuts out an event-related potential in a predetermined zone (e.g., a zone from 100 ms before the presentation of the first sound to 400 ms after the presentation of the third sound), and sends that waveform data to the extraction section 55.

An event-related potential is a fluctuation in the potential of an electroencephalogram that occurs in response to a stimulation. The event-related potential comes in different event-related potential types, depending on: (1) the polarity of potential (plus or minus); (2) the latency (the time from occurrence of a stimulation and until occurrence of a potential fluctuation); (3) the amplitude level of potential; and so on. Each different type of signal contains different information concerning the user 5.

In the case where a band-pass filter is used as the frequency filter, the cutoff frequency may be set so as to pass e.g. 5 Hz to 15 Hz. It is assumed that the user 5 has worn the electroencephalograph in advance. The probe electrode for electroencephalogram measurement is attached at the central portion Cz, for example.

<Event-Related Potential Characteristic Amount Extraction Section 55 (Extraction Section 55)>

In accordance with the particulars of the sound stimulations received from the sound pressure determination section 71, the extraction section 55 acquires waveform data of the event-related potential received from the biological signal measurement section 50, and calculates wavelet-coefficient related characteristic amounts in response to the first sound to the third sound.

The extraction section 55 sends the calculated characteristic amounts and the sound stimulation information (right or left ear, frequency, sound pressure, etc.) to the determination section 65. Each wavelet-coefficient related characteristic amount may be derived as an average value of wavelet coefficients over a predetermined range on each of the frequency axis and the time axis, for example. For instance, an average may be taken over a range from 5 Hz to 15 Hz on the frequency axis and over a time range of 50 ms on the time axis.

Furthermore, as a P2 component of event-related potential for characteristic amount calculation, for example, a biological signal in a time range of 300 ms or less after an auditory stimulation from the point of auditory stimulation may be used. So long as uncomfortable sound pressure estimation is possible, the ranges on the frequency axis and the time axis over which averaging is to be conducted for characteristic amount calculation may be finer or coarser than 5 Hz to 15 Hz and every 50 ms, respectively.

Alternatively, as an N1 component of event-related potential for characteristic amount calculation, for example, a negative-component biological signal in a time range of 50 ms to 150 ms after presentation of an auditory stimulation may be used. For example, a P2-component of the event-related potential for characteristic amount calculation may be a positive-component biological signal in a time range of 150 ms to 250 ms after an auditory stimulation.

<Uncomfortable Sound Pressure Determination Section 65 (Determination Section 65)>

The determination section 65 refers to the characteristic amounts of the respective sound stimulations of the first sound, second sound, and third sound as extracted by the extraction section 55 (e.g., wavelet coefficients), as well as a predetermined criterion which previously defines association between characteristic amounts and uncomfortable sound pressure values, and determines an uncomfortable sound pressure of the user 5.

Specifically, the determination section 65 determines an uncomfortable sound pressure in view of the characteristic amounts for the respective sound stimulations (e.g., wavelet-coefficient related characteristic amounts for the respective ones of the first sound to the third sound) received from the extraction section 55. The determination section 65 conducts linear discrimination by using a predetermined criterion and wavelet characteristic amounts prepared in advance.

The "predetermined criterion" means information which previously defines association between characteristic amounts and uncomfortable sound pressure values. The "predetermined criterion" may be a table which previously defines association between wavelet characteristic amounts and uncomfortable sound pressure values, or a predetermined formula (mathematical function), for example. The determination section 65 retains the predetermined criterion in advance.

The aforementioned "predetermined criterion" is training data for subjective UCL values, for example. The training data can be generated from subjective UCL values and wavelet characteristic amounts that are measured by previously conducting the aforementioned subjective report experiment and electroencephalogram measurement experiment for at least two or more other people.

Herein, the sound stimulation conditions concerning the sound pressure and number of sound stimulations in the electroencephalogram measurement experiment when generating the training data need to identically conform to the pattern of changing stimulation sound pressure as determined by the sound pressure determination section 71, in the case where successive sounds are presented as the sound stimulations. The training data may be retained so as to be itemized for each of the right or left ear and for each frequency, as shown in FIG. 6, for example. In that case, based on the sound information received from the extraction section 55 (e.g., information of the right or left ear to which the sound stimulations are presented and sound stimulation frequency), the training data which is utilized for uncomfortable sound pressure estimation may be switched so that the right or left ear and frequency of the training data match the right or left ear and frequency of the one who is the subject of determination. Moreover, the training data may be switched according to the user's symptoms of hypacusia. For example, training data may be prepared and switched between general categories, e.g., conductive deafness and perceptive deafness. Also, training data may be prepared and switched according to the audiogram pattern, e.g., gradual low tone loss or gradual high tone loss. The determination section 65 sends the determined uncomfortable sound pressure to the result accumulating database (DB) 80.

<Result Accumulating Database (DB) 80>

The result accumulating DB 80 stores the uncomfortable sound pressure received from the determination section 65 in association with the right or left ear and each frequency as indicated by the sound stimulation group information received from the sound stimulation group determination section 70. FIG. 12 shows an example of data accumulation in the result accumulating DB 80. FIG. 12 illustrates a case where an uncomfortable sound pressure is accumulated with respect to each of the right or left ear and each different frequency. Although FIG. 12 illustrates uncomfortable sound pressures corresponding to three frequencies, this is an example. As shown in FIG. 11, uncomfortable sound pressures corresponding to 250 Hz and 500 Hz may be included.

<Processing by the Estimation System 100>

Figure 13:
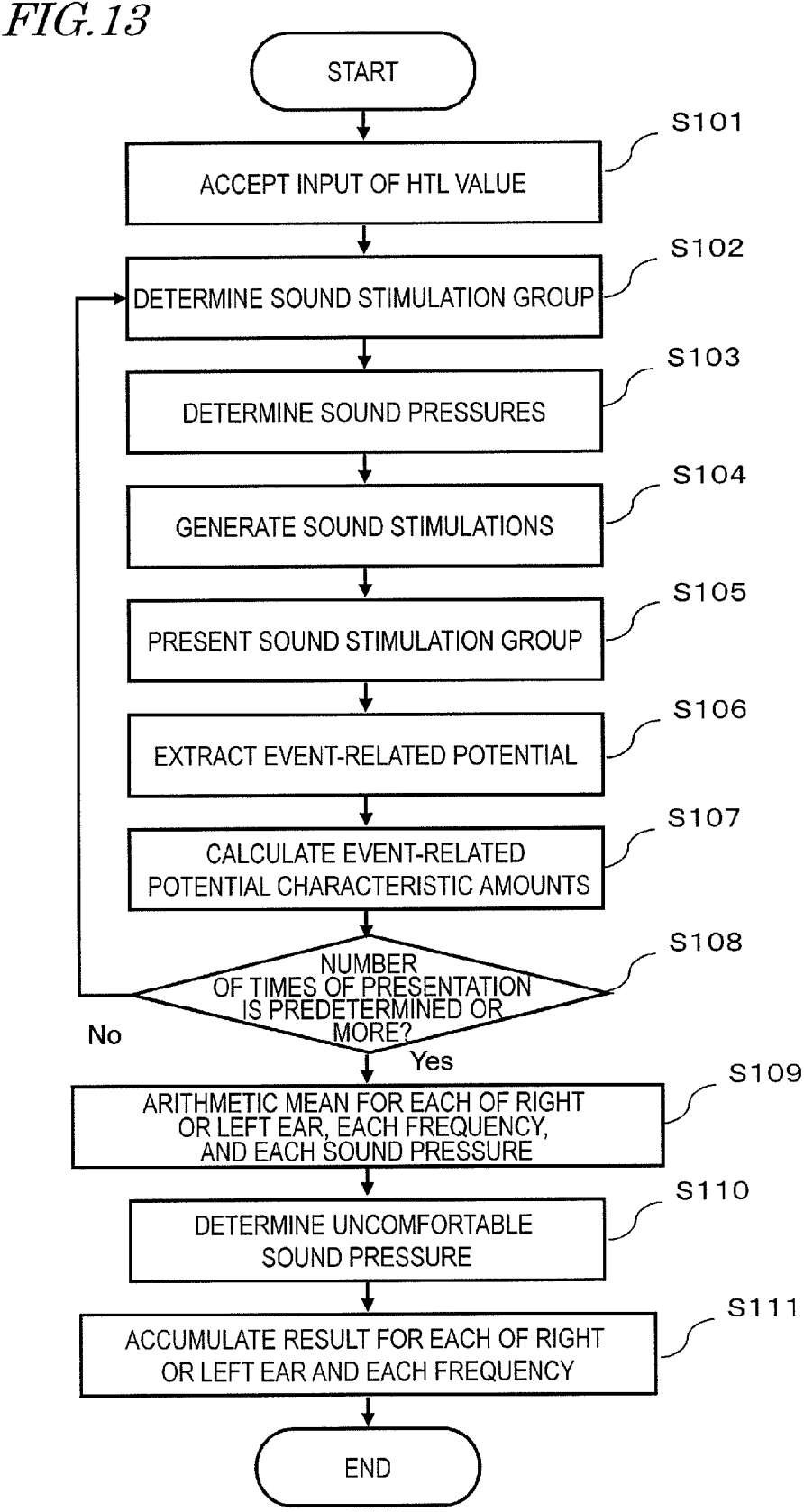
FIG. 13 is a flowchart showing overall processing by the uncomfortable sound pressure estimation system in outline.

Next, with reference to FIG. 13, a processing procedure which is performed by the estimation system 100 of FIG. 10 will be described. FIG. 13 is a flowchart showing a procedure of processing performed in the estimation system 100.

At step S101, from the user or evaluator, the HTL input section 90 accepts input of the user's HTL value for each of the right or left ear and for each frequency, and sends that information to the sound pressure determination section 71.

At step S102, the sound stimulation group determination section 70 determines the ear to which the sound stimulation group is presented, frequency, duration of each sound stimulation in the sound stimulation group, and interval between stimulations. The frequency and the ear for which to present the sound stimulation may be randomly decided under the following constraints, for example.

No sound stimulation of the same frequency as that of an immediately previous sound stimulation group is selected.

The ear is selected in random order between right and left; however, not more than four sound stimulation groups are successively presented to either the right or left ear.

The duration of a sound stimulation is set to be e.g. 25 ms or more, so that an auditory evoked potential is stably induced. The interval between stimulations is set to a time which is equal to or greater than the duration of the sound stimulation but equal to or less than 1 second. For example, it may be 300 ms, or 200 ms. To the sound pressure determination section 71, the sound stimulation group determination section 70 sends the determined information of the ear to which the sound stimulation group is presented, frequency, duration of each sound stimulation in the sound stimulation group, and interval between stimulations.

At step S103, from the sound stimulation group determination section 70, the sound pressure determination section 71 receives the information of the ear to which the sound stimulation group is presented, frequency, duration of each sound stimulation in the sound stimulation group, and interval between stimulations. Moreover, from the HTL input section 90, the sound pressure determination section 71 receives the user's HTL value for each of the right or left ear and for each frequency. Then, the sound pressure determination section 71 determines the sound pressures of the first sound to the third sound in the sound stimulation group so as to constitute monotonously descending sound pressures in a sound pressure range higher than the HTL and lower than a sound pressure which is generally evaluated to be the UCL. For example, if the HTL value for a given frequency is 50 dBHL, the sound pressure of the first sound may be determined to be 80 dBHL, the sound pressure of the second sound to be 75 dBHL, and the sound pressure of the third sound to be 70 dBHL. Alternatively, the sound pressure of the first sound may be determined to be 80 dBHL, the sound pressure of the second sound to be 70 dBHL, and the sound pressure of the third sound to be 60 dBHL. Together with the information received from the sound stimulation group determination section 70, the sound pressure determination section 71 sends the determined sound pressure information for each sound stimulation in the sound stimulation group to the sound stimulation generation section 75.

At step S104, based on the sound stimulation information received from the sound pressure determination section 71, the sound stimulation generation section 75 generates sound stimulation data. Each sound stimulation may be a tone burst sound with a rise and fall of 3 ms, for example.

At step S105, the sound stimulation generation section 75 presents the sound stimulation group to the user via the sound stimulation output section 10, and at that timing outputs a trigger signal to the biological signal measurement section 50. The sound stimulation data may be generated in such a manner that a single piece of sound stimulation data is created for one sound stimulation group, from which a plurality of sound stimulations that undergo changes in sound pressure at a predetermined time interval are derived, for example. In that case, the trigger signal to be sent to the biological signal measurement section 50 may only be sent at the timing of presenting the first sound.

At step S106, the biological signal measurement section 50 measures an electroencephalogram as a biological signal. Then, it applies frequency filtering with an appropriate cutoff frequency to the electroencephalogram data, and based on the trigger received from the sound stimulation generation section 75 as a starting point, cuts out an event-related potential in a predetermined zone (e.g., a zone from 100 ms before the presentation of the first sound to 400 ms after the presentation of the $n^{th}$ sound), and sends the waveform data of this event-related potential to the extraction section 55.

At step S107, from the event-related potential received from the biological signal measurement section 50, the extraction section 55 extracts wavelet-coefficient related characteristic amounts in response to the first sound to the third sound, in accordance with the particulars of the sound stimulations received from the sound pressure determination section 71.

In the case where an event-related potential is cut out in a zone from 100 ms before the presentation of the first sound to 400 ms after the presentation of the $n^{th}$ sound as is mentioned above, the extraction section 55 is able to calculate wavelet coefficients from this single piece of event-related potential data. From the calculated wavelet coefficients, the extraction section 55 is able to extract the respective wavelet-coefficient related characteristic amounts in response to the first sound to the third sound based on time and frequency. The extracted wavelet-coefficient related characteristic amounts in response to the first sound to the third sound are accumulated in a storage device such as a memory (not shown).

Although the present embodiment illustrates that the wavelet-coefficient related characteristic amounts in response to the first sound to the third sound are each extracted, this is an example. Extraction of the characteristic amount in response to the first sound may be omitted. As shown in FIG. 5, the wavelet coefficients for the second sound and the third sound reflect the difference in subjective UCL value. Therefore, in uncomfortable sound pressure determination, it suffices if the wavelet coefficient(s) for the second sound and/or third sound is available.

At step S108, the sound stimulation group determination section 70 determines whether the number of times of presentation of the sound stimulation group has reached a predetermined number of times. The predetermined number of times may be 20 times, for example. Note that "20 times" is a mere example, although it is a number of summations which is frequently adopted in fields where event-related potentials are to be measured.

If the number of times of presentation is less than the predetermined number of times, the process returns to step S102 to repeat the processes of step S102 and after. If the number of times of presentation is equal to or greater than the predetermined number of times, the process proceeds to step S109.

At step S109, the extraction section 55 takes an arithmetic mean of the wavelet-coefficient related characteristic amounts in response to the first sound to the third sound which have been accumulated in the storage device through the predetermined number or more trials, based on the sound stimulation information received from the sound pressure determination section 71. The arithmetic mean is taken for each of the first sound, the second sound, or the third sound, and for each of these, taken for each of the right or left ear and for each frequency.

The extraction section 55 sends the arithmetic-meaned wavelet-coefficient related characteristic amounts to the determination section 65, and the process proceeds to step S110.

At step S110, the determination section 65 determines an uncomfortable sound pressure by using the respective wavelet-coefficient related characteristic amounts in response to the first sound to the third sound received from the extraction section 55. The uncomfortable sound pressure determination is achieved through linear discrimination, by using the wavelet characteristic amounts of other people and training data for subjective UCL values that are previously prepared.

The training data which is utilized for uncomfortable sound pressure estimation may be switched so that the right or left ear and frequency of the training data match the right or left ear and frequency of the one who is the subject of determination. Moreover, the training data may be switched according to the user's symptoms of hypacusia. For example, training data may be prepared and switched between general categories, e.g., conductive deafness and perceptive deafness. Also, training data may be prepared and switched according to the audiogram pattern, e.g., gradual low tone loss or gradual high tone loss.

At step S111, the result accumulating DB 80 accumulates the information of a result of uncomfortable sound pressure determination that is received from the determination section 65 for each of the right or left ear and for each frequency of the sound stimulation group presented at step S105.

The estimation system 100 of the present embodiment presents pure tones of the same frequency three times in succession at monotonously ascending or monotonously descending sound pressures, extracts electroencephalographic characteristic amounts in response to the respective sound stimulations of the first to third sounds, and measures an uncomfortable sound pressure from a change pattern of the characteristic amounts. This realizes a hearing aid fitting which does not allow the user to experience an uncomfortable sound pressure upon wearing a hearing aid.

In the description of the present embodiment, it is illustrated that the biological signal measurement section 50 cuts out an event-related potential in a predetermined range based on a trigger from the sound stimulation generation section 75 as a starting point, and sends it to the extraction section 55. However, this process is an example. In another process, for example, the biological signal measurement section 50 may constantly measure an electroencephalogram, and the extraction section 55 may perform cutting out of an event-related potential and a baseline correction as needed. With such a construction, the sound stimulation generation section 75 does not need to send a trigger to the biological signal measurement section 50, but may only send a trigger to the extraction section 55.

Although the present embodiment illustrates that the results of uncomfortable sound pressure estimation are accumulated in the result accumulating DB 80, accumulation is not necessary. For example, in the case where the result accumulating DB 80 is provided external to the uncomfortable sound pressure estimation apparatus 1, each result of determination of the determination section 65 may simply be output. Each result of determination can be utilized as information concerning uncomfortable sound pressure.

Figure 14:
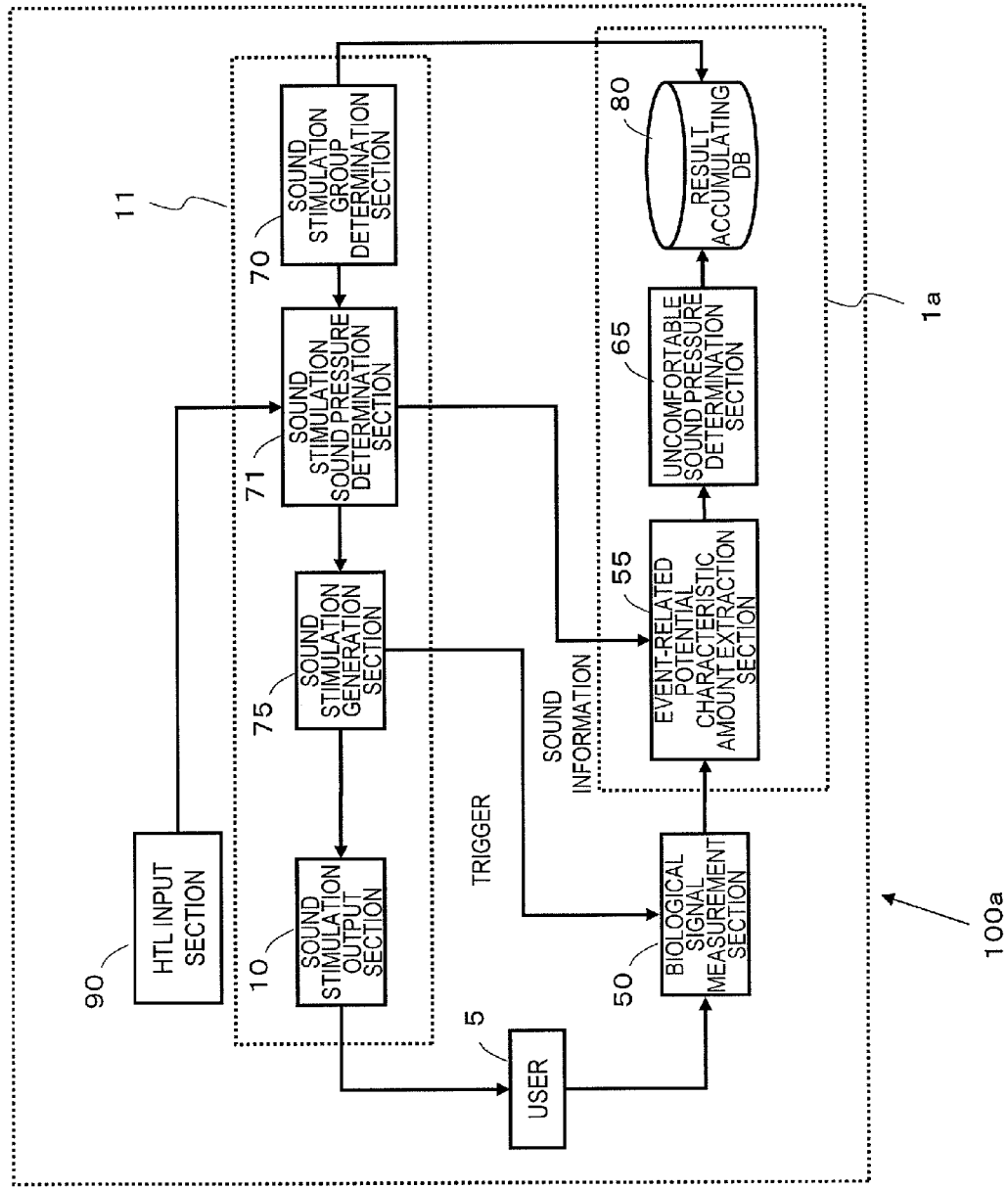
FIG. 14 shows a variant of the construction of Embodiment 1.

Moreover, the relationship between the system 100 and the uncomfortable sound pressure estimation apparatus 1 as a component element thereof, illustrated in FIG. 10, is also a mere example. For example, FIG. 14 shows an example of an uncomfortable sound pressure estimation system 100a which includes an uncomfortable sound pressure estimation apparatus 1a and a sound stimulation apparatus 11. The uncomfortable sound pressure estimation apparatus 1a is a version of the uncomfortable sound pressure estimation apparatus 1 (FIG. 10) from which the sound stimulation group determination section 70, the sound pressure determination section 71, and the sound stimulation generation section 75 are omitted. The sound stimulation apparatus 11 includes the sound stimulation group determination section 70, the sound pressure determination section 71, the sound stimulation generation section 75, and the sound stimulation output section 10 shown in FIG. 10. The sound stimulation apparatus 11 and the uncomfortable sound pressure estimation apparatus 1a are connected to the uncomfortable sound pressure estimation apparatus 1 in a wired or wireless manner to perform exchange of information.

Embodiment 2

In the present embodiment, similarly to Embodiment 1, sound stimulations of sound pressures that are lower than a sound pressure which is generally evaluated to be the UCL are presented a plurality of times in succession, at monotonously descending sound pressures. Then, an uncomfortable sound pressure measurement system which uses an N1-P2 amplitude in response to each sound stimulation to measure the presence or absence tolerance against sounds of high sound pressure will be described.

Figure 17:
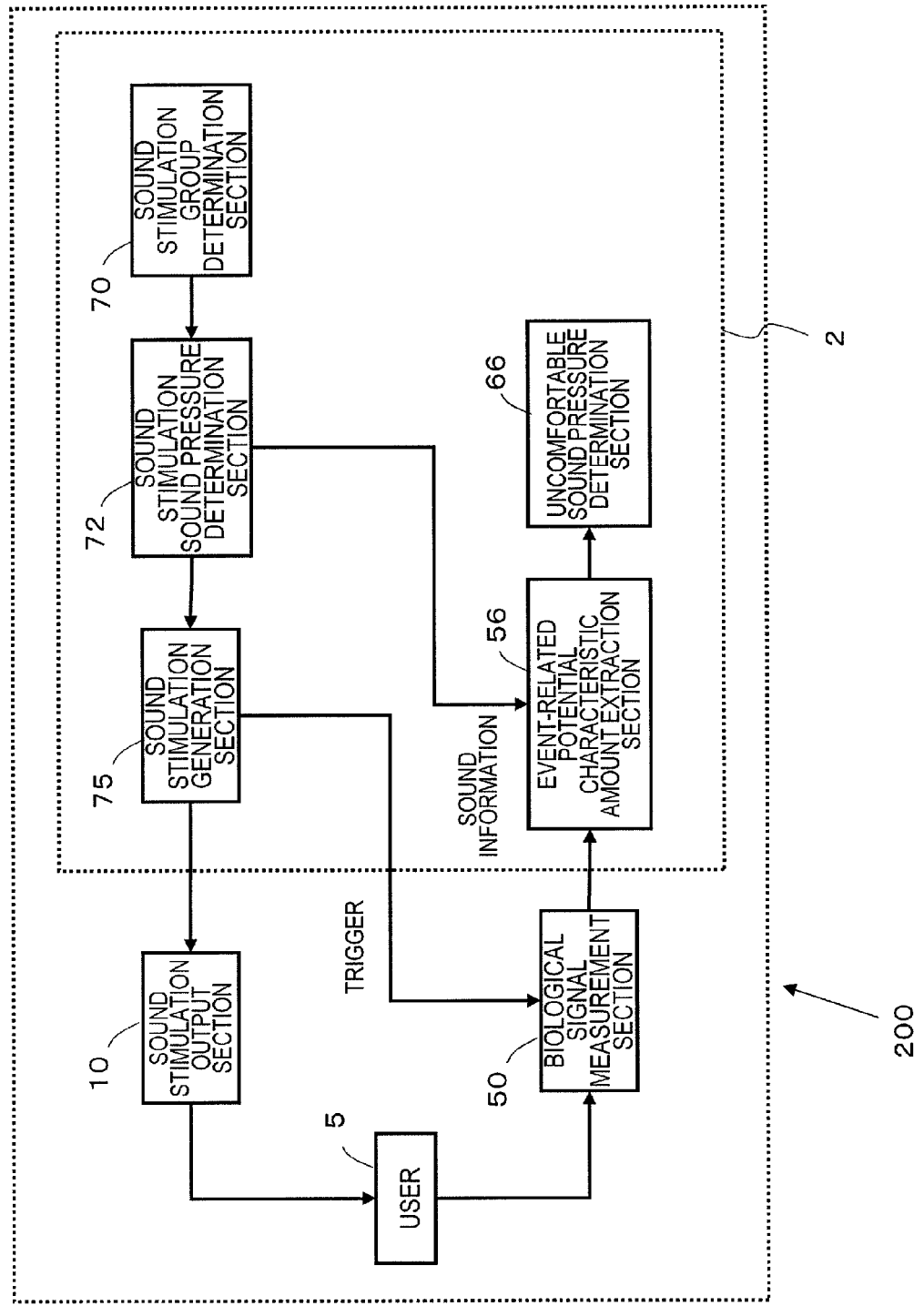
FIG. 17 shows the construction of an uncomfortable sound pressure measurement system according to Embodiment 2.

FIG. 17 shows the functional block construction of an uncomfortable sound pressure measurement system 200 according to the present embodiment. The uncomfortable sound pressure estimation system 200 (hereinafter referred to as the "estimation system 200") includes a sound stimulation output section 10, a biological signal measurement section 50, and an uncomfortable sound pressure estimation apparatus 2. Blocks which are identical to those in FIG. 10 showing the construction of Embodiment 1 will be denoted by like numerals, and their description will be omitted. Note that the hardware construction of the uncomfortable sound pressure estimation apparatus 2 is as shown in FIG. 9. As a program which defines different processes from the program 35 described in Embodiment 1 is executed, the uncomfortable sound pressure estimation apparatus 2 of the present embodiment as shown in FIG. 17 is realized.

The uncomfortable sound pressure estimation apparatus 2 of the present embodiment differs from the uncomfortable sound pressure estimation apparatus 1 of Embodiment 1 in that an uncomfortable sound pressure determination section 66 (hereinafter the "determination section 66") is provided, instead of the determination section 65. Although the names of the component element of the uncomfortable sound pressure estimation apparatus 2 are primarily identical to those of the uncomfortable sound pressure estimation apparatus 1 of Embodiment 1, reference numerals are used where any different operation and/or function is possessed. Therefore, the event-related potential characteristic amount extraction section 56 (hereinafter the "extraction section 56") and the sound stimulation sound pressure determination section 72 (hereinafter the "sound pressure determination section 72") according to the present embodiment differ from the extraction section 55 and the sound pressure determination section 71 of Embodiment 1 in terms of operation and/or function. Although FIG. 17 illustrates that the uncomfortable sound pressure estimation apparatus 2 does not include the sound stimulation output section 10, this construction is an example. For example, an uncomfortable sound pressure estimation apparatus 2 which at least includes the sound stimulation output section 10, the extraction section 56, and the determination section 66 may be provided. These component elements can be accommodated in a single housing to be operated as a single uncomfortable sound pressure estimation apparatus.

Hereinafter, the extraction section 56, the determination section 66, and the sound pressure determination section 72 will be described.

From the sound stimulation group determination section 70, the sound pressure determination section 72 receives the information of the ear to which the sound stimulation group is presented (the right ear or the left ear), frequency, duration of each sound stimulation in the sound stimulation group, and interval between stimulations. Then, it determines the sound pressures of the first sound to the third sound in the sound stimulation group so as to constitute monotonously descending sound pressures in a sound pressure range lower than a sound pressure which is generally evaluated to be the UCL. For example, the sound pressure of the first sound may be determined to be 80 dBHL, the sound pressure of the second sound to be 75 dBHL, and the sound pressure of the third sound to be 70 dBHL.

From the event-related potential received from the biological signal measurement section 50, the extraction section 56 calculates N1-P2-amplitude related characteristic amounts in response to the second sound and the third sound, in accordance with the particulars of the sound stimulations received from the sound pressure determination section 71. The N1-P2 amplitude is determined as the absolute value of a difference between an N1 amplitude and a P2 amplitude. For example, the N1 amplitude may be a zone average potential from 90 ms to 110 ms after presenting each of the sound stimulations of the first sound to the third sound, or a peak amplitude. For example, the P2 amplitude may similarly be a zone average potential from 190 ms to 210 ms after sound stimulation presentation, or a peak amplitude. Then, the calculated characteristic amounts and the sound stimulation information (right or left ear, frequency, sound pressure, etc.) are sent to the determination section 66.

For the respective N1-P2-amplitude related characteristic amounts in response to the second sound and the third sound received from the extraction section 56, the determination section 66 makes a coarse uncomfortable sound pressure determination (high/low). Specifically, a threshold value is provided for each frequency and each of the second sound/third sound, and, if the measured N1-P2 amplitude of the second sound/third sound is greater than the threshold value(s), the uncomfortable sound pressure is determined to be high; and if it is smaller than the threshold value(s), the uncomfortable sound pressure is determined to be low. Note that the uncomfortable sound pressure may be determined to be high when both of the N1-P2 amplitudes in response to the second sound and the third sound are greater than the threshold values; or the uncomfortable sound pressure may be determined to be high when either amplitude is greater than the threshold value. Examples of threshold values for different frequencies and each of the second sound/third sound are shown in FIG. 18. As exemplary threshold values, FIG. 18 indicates an average value, between the case where the subjective UCL value shown in FIG. 16 is greater than 95 dBHL and the case where it is equal to or less than 95 dBHL, of N1-P2 amplitude for each frequency.

Next, with reference to the flowchart of FIG. 19, an overall procedure of processing performed in the estimation system 200 will be described.

Figure 19:
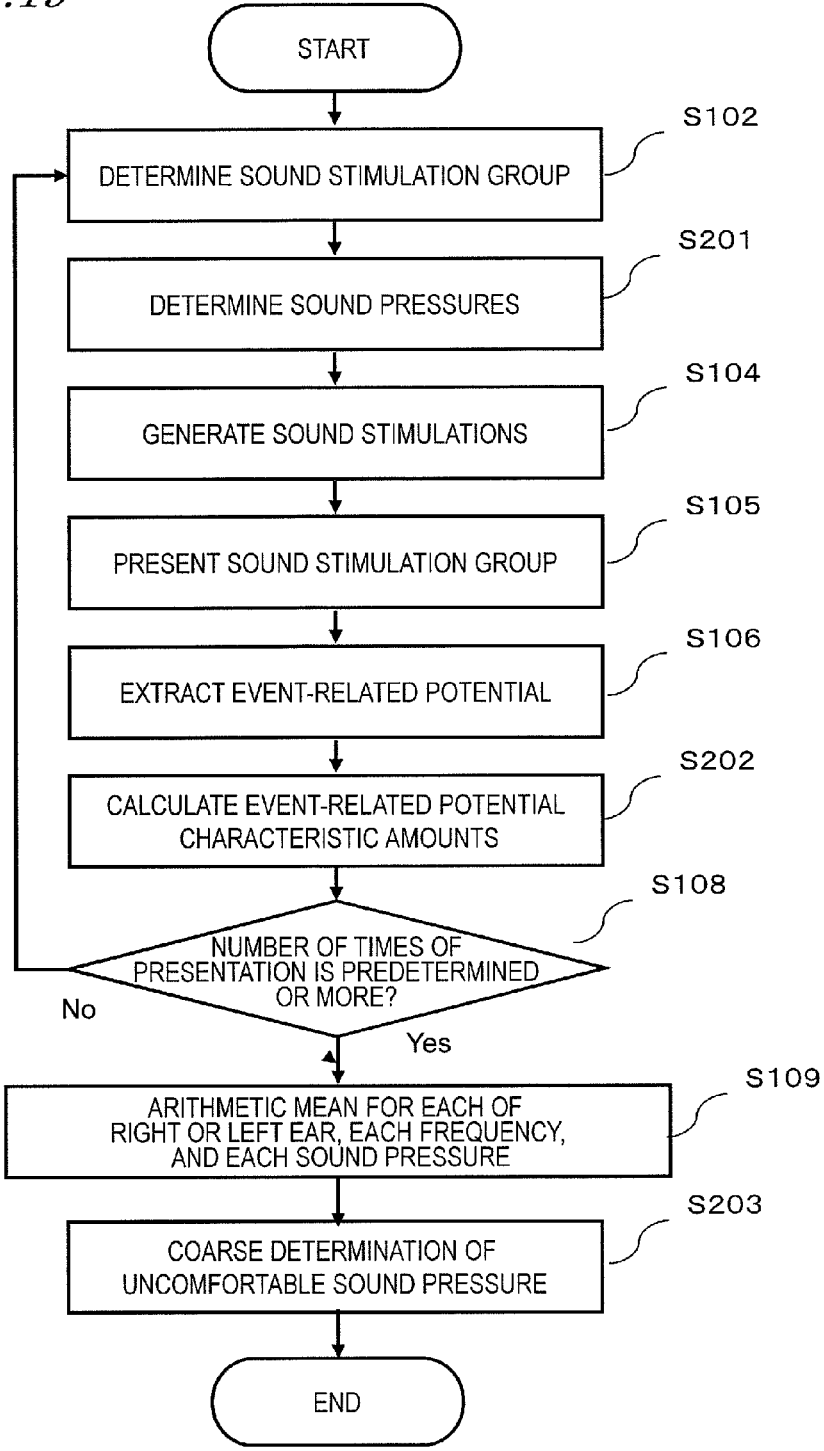
FIG. 19 is a flowchart showing overall processing by the uncomfortable sound pressure measurement system in outline.

FIG. 19 is a flowchart showing a procedure of processing by the estimation system 200 of the present embodiment. In FIG. 19, steps of conducting identical processes to the processes of the estimation system 100 (FIG. 13) will be denoted by like reference numerals, and their description will be omitted.

The processing by the estimation system 200 of the present embodiment differs from the processing by the uncomfortable sound pressure measurement system 100 of Embodiment 1 with respect to steps S201, S202, and S203. Steps S201 to step S203 will be described below.

At step S201, the sound pressure determination section 72 receives the information of the ear to which the sound stimulation group is presented (the right ear or the left ear), frequency, duration of each sound stimulation in the sound stimulation group, and interval between stimulations from the sound stimulation group determination section 70. Then, it determines the sound pressures of the first sound to the third sound in the sound stimulation group so as to constitute monotonously descending sound pressures in a sound pressure range lower than a sound pressure which is generally evaluated to be the UCL. For example, the sound pressure of the first sound may be determined to be 80 dBHL, the sound pressure of the second sound to be 75 dBHL, and the sound pressure of the third sound to be 70 dBHL.

At step S202, from the event-related potential received from the biological signal measurement section 50, the extraction section 56 calculates N1-P2-amplitude related characteristic amounts in response to the second sound and the third sound, in accordance with the particulars of the sound stimulations received from the sound pressure determination section 71. The N1-P2 amplitude is determined as the absolute value of a difference between an N1 amplitude and a P2 amplitude. For example, the N1 amplitude may be a zone average potential from 90 ms to 110 ms after presenting each of the sound stimulations of the first sound to the third sound, or a peak amplitude. For example, the P2 amplitude may similarly be a zone average potential from 190 ms to 210 ms after sound stimulation presentation, or a peak amplitude. Then, the calculated characteristic amounts and the sound stimulation information (right or left ear, frequency, sound pressure, etc.) are sent to the determination section 66.

At step S203, for the respective N1-P2-amplitude related characteristic amounts in response to the second sound and the third sound received from the extraction section 56, the determination section 66 makes a coarse uncomfortable sound pressure determination (high/low). Specifically, a threshold value is provided for each frequency and each of the second sound/third sound, and, if the measured N1-P2 amplitude of the second sound/third sound is greater than the threshold value(s), the uncomfortable sound pressure is determined to be high; and if it is smaller than the threshold value(s), the uncomfortable sound pressure is determined to be low.

Through such processes, without performing complicated calculations such as wavelet coefficient calculation or linear discrimination, it is possible to make a coarse determination as to whether the uncomfortable sound pressure is high or not. The uncomfortable sound pressure being high would mean that the user has tolerance against sounds of high sound pressure, and the uncomfortable sound pressure being low would mean that he or she lacks tolerance against sounds of high sound pressure.

In accordance with the estimation system 200 of the present embodiment, sound stimulations of sound pressures that are lower than a sound pressure which is generally evaluated to be the UCL are presented a plurality of times in succession at monotonously descending sound pressures, and based on N1-P2 amplitudes in response to the second sound and the third sound, a simple determination can be made as to whether the user has tolerance against sounds of high sound pressure or not. This would make it possible to automatically reduce the sound volume of a hearing aid or audio player if there is no tolerance against sounds of high sound pressure.

The uncomfortable sound pressure estimation apparatuses according to the embodiments and variants above may each be implemented as a semiconductor chip circuit. Instead of a semiconductor chip circuit, it may be implemented as a CPU which is provided within a PC. By executing a computer program, the CPU is able to realize the function of each component element.

In accordance with the uncomfortable sound pressure estimation system of the present invention, an uncomfortable sound pressure of a user can be estimated without presenting any overbearing sound stimulations, which is useful for adjustment of a hearing aid at a hearing aid shop or in households, etc. Moreover, by estimating an uncomfortable sound pressure for a person with normal hearing in advance, it is also applicable to the setting of a maximum sound volume in an audio device such as a television set or a stereo set, and so on.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An uncomfortable sound pressure estimation system comprising:
 a biological signal measurement section configured to measure an electroencephalogram signal of a user;
 a sound stimulation output section configured to present a sound stimulation group to the user, the sound stimulation group including a first sound, a second sound, and a third sound which are pure tones of a same frequency and which consecutively decrease in sound pressure within a predetermined range, so as to constitute monotonously descending sound pressures in a sound pressure range higher than a hearing threshold level (HTL) and lower than a sound pressure which is generally evaluated to be an uncomfortable level (UCL);
 an extraction section configured to extract, from the electroencephalogram signal in a predetermined zone defined based on a point of presenting at least one of the second sound and the third sound as a starting point, an N1-P2-amplitude related or wavelet-coefficient related characteristic amount of event-related potential of the electroencephalogram signal; and
 a determination section configured to determine an uncomfortable sound pressure at the frequency of the sound stimulation group based on the characteristic amount extracted by the extraction section.

2. The uncomfortable sound pressure estimation system of claim 1, wherein the determination section determines the uncomfortable sound pressure by referring to a predetermined criterion which previously defines association between characteristic amounts and uncomfortable sound pressure values.

3. The uncomfortable sound pressure estimation system of claim 1, further comprising:
 a sound stimulation group determination section configured to determine the frequency of the sound stimulation group; and
 a sound pressure determination section configured to determine sound pressures of the first sound, the second sound, and the third sound so as to consecutively decrease within the predetermined range, wherein,
 the sound stimulation output section outputs the first sound, the second sound, and the third sound at the frequency determined by the sound stimulation group determination section and at the sound pressures determined by the sound pressure determination section.

4. The uncomfortable sound pressure estimation system of claim 3, wherein the sound pressure determination section determines the sound pressures of the sound stimulation group to be sound pressures which are lower than a predetermined threshold value.

5. The uncomfortable sound pressure estimation system of claim 3, wherein the sound pressure determination section determines the sound pressures of the sound stimulation group to be sound pressures higher than a hearing threshold level of the user.

6. The uncomfortable sound pressure estimation system of claim 1, wherein the sound stimulation output section outputs the sound stimulation group so that the first sound, the second sound, and the third sound decrease by every 5 dB or decrease by every 10 dB.

7. The uncomfortable sound pressure estimation system of claim 1, wherein the determination section retains a predetermined criterion which previously defines association between N1-P2 amplitude or wavelet characteristic amounts and uncomfortable sound pressure values, and determines the uncomfortable sound pressure by making a linear discrimination using the characteristic amount extracted by the extraction section and the predetermined criterion.

8. The uncomfortable sound pressure estimation system of claim 7, wherein,
when the determination section retains a predetermined criterion which defines association between N1-P2 amplitudes and uncomfortable sound pressure values, the extraction section extracts an N1-P2-amplitude related characteristic amount of event-related potential of the electroencephalogram signal; and
when the determination section retains a predetermined criterion which previously defines association between wavelet characteristic amounts and uncomfortable sound pressure values, the extraction section extracts a wavelet-coefficient related characteristic amount.

9. The uncomfortable sound pressure estimation system of claim 1, wherein the determination section retains the predetermined criterion for each of a right or left ear and for each frequency, and switches the criterion to be used depending on the right or left ear and frequency of the sound stimulation group.

10. The uncomfortable sound pressure estimation system of claim 1, wherein the extraction section calculates a wavelet coefficient of an electroencephalogram signal in a zone defined as a point of time of 350 ms or less from the point of presenting each of the first sound to the third sound, and defines a value obtained through averaging over a predetermined frequency range and a predetermined time range as a characteristic amount.

11. The uncomfortable sound pressure estimation system of claim 10, wherein the predetermined frequency range is between 5 Hz and 12.5 Hz.

12. The uncomfortable sound pressure estimation system of claim 10, wherein the predetermined time range is 50 ms.

13. The uncomfortable sound pressure estimation system of claim 4, wherein a HTL value defines the smallest sound pressure of a pure tone that allows the pure tone to be heard by the user, and the predetermined threshold value is 90 dBHL when the HTL value is 20 dBHL or less; 95 dBHL when the HTL value is 50 dBHL or less; 100 dBHL when the HTL value is 65 dBHL or less; 105 dBHL when the HTL value is 75 dBHL or less; 115 dBHL when the HTL value is 90 dBHL or less; and 120 dBHL when the HTL value is 95 dBHL or more.

14. The uncomfortable sound pressure estimation system of claim 4, further comprising an input section to which a hearing threshold level of the user is input.

15. An uncomfortable sound pressure estimation system comprising:
a biological signal measurement section configured to measure an electroencephalogram signal of a user;
a sound stimulation output section configured to present a sound stimulation group to the user, the sound stimulation group including a first sound, a second sound, and a third sound which are pure tones of a same frequency and which consecutively decrease in sound pressure within a predetermined range, so as to constitute monotonously descending sound pressures in a sound pressure range higher than a hearing threshold level (HTL) and lower than a sound pressure which is generally evaluated to be an uncomfortable level (UCL);
an extraction section configured to extract, in the electroencephalogram signal measured by the biological signal measurement section, a characteristic amount concerning event-related potential of the electroencephalogram signal in a predetermined zone defined based on a point of presenting at least one of the second sound and the third sound as a starting point; and
a determination section configured to determine an uncomfortable sound pressure at the frequency of the sound stimulation group based on the characteristic amount extracted by the extraction section.

16. An uncomfortable sound pressure estimation method comprising:
measuring an electroencephalogram signal of a user;
presenting a sound stimulation group to the user, the sound stimulation group including a first sound, a second sound, and a third sound which are pure tones of a same frequency and which consecutively decrease in sound pressure within a predetermined range, so as to constitute monotonously descending sound pressures in a sound pressure range higher than a hearing threshold level (HTL) and lower than a sound pressure which is generally evaluated to be an uncomfortable level (UCL);
from the electroencephalogram signal in a predetermined zone defined based on a point of presenting at least one of the second sound and the third sound as a starting point, extracting an N1-P2-amplitude related or wavelet-coefficient related characteristic amount of event-related potential of the electroencephalogram signal; and
determining an uncomfortable sound pressure at the frequency of the sound stimulation group based on the extracted characteristic amount.

17. A non-transitory computer-readable medium having stored thereon a computer program to be executed by a computer mounted in an uncomfortable sound pressure estimation apparatus of an uncomfortable sound pressure estimation system,
wherein the computer program causes the computer to execute:
acquiring an electroencephalogram signal of a user;
presenting a sound stimulation group to the user, the sound stimulation group including a first sound, a second sound, and a third sound which are pure tones of a same frequency and which consecutively decrease in sound pressure within a predetermined range, so as to constitute monotonously descending sound pressures in a sound pressure range higher than a hearing threshold level (HTL) and lower than a sound pressure which is generally evaluated to be an uncomfortable level (UCL);

from the electroencephalogram signal in a predetermined zone defined based on a point of presenting at least one of the second sound and the third sound as a starting point, extracting an N1-P2-amplitude related or wavelet-coefficient related characteristic amount of event-related potential of the electroencephalogram signal; and determining an uncomfortable sound pressure at the frequency of the sound stimulation group based on the extracted characteristic amount.

* * * * *